(12) United States Patent
Takesako et al.

(10) Patent No.: US 7,070,793 B1
(45) Date of Patent: Jul. 4, 2006

(54) ANTIGEN PROTEIN AND NUCLEIC ACID CODING FOR SAID PROTEIN

(75) Inventors: Kazutoh Takesako, Otsu (JP);
Shigetoshi Mizutani, Shiga (JP);
Masahiro Endo, Kusatsu (JP); Junko Ogawa, Otsu (JP); Takashi Okado, Kyoto (JP); Ikunoshin Kato, Uji (JP)

(73) Assignee: Takara Bio, Inc., Otsu (JP)

( * ) Notice: Subject to any disclaimer, the term of this patent is extended or adjusted under 35 U.S.C. 154(b) by 0 days.

(21) Appl. No.: 09/509,744

(22) PCT Filed: Sep. 28, 1998

(86) PCT No.: PCT/JP98/04326

§ 371 (c)(1),
(2), (4) Date: Mar. 31, 2000

(87) PCT Pub. No.: WO99/16881

PCT Pub. Date: Apr. 8, 1999

(30) Foreign Application Priority Data

Oct. 1, 1997 (JP) ............................. 9-269087

(51) Int. Cl.
A61K 39/00 (2006.01)
A61K 39/02 (2006.01)
C07K 1/00 (2006.01)
C12N 15/00 (2006.01)
C12N 15/09 (2006.01)

(52) U.S. Cl. .................. 424/274.1; 424/185.1; 424/200.1; 530/350; 530/824; 435/320.1; 435/71.1; 435/69.3; 514/2; 536/23.74; 536/23.7

(58) Field of Classification Search .......... 530/350, 530/300, 824, 820, 806; 514/2; 536/23.7, 536/23.1, 23.74; 935/66, 69, 72; 435/320.1, 435/71.1, 69.3; 424/185.1, 200.1, 184.1, 424/192.1, 274.1
See application file for complete search history.

(56) References Cited

U.S. PATENT DOCUMENTS 4,753,888 A * 6/1988 Chiang ..................... 436/11
5,541,077 A * 7/1996 Burnie et al. .............. 435/7.31
6,277,564 B1 * 8/2001 Berlin et al. ................ 435/6

FOREIGN PATENT DOCUMENTS

JP 10234379 A * 9/1998
WO A1-9636707 11/1996

OTHER PUBLICATIONS

Houghten et al. In: New Approaches to immunization. Vaccines86, (Ed) Brown et al., Cold Spring Harbor Laboratory, pp. 21–25, 1986.*
Mirande et al. J. Biol. Chem. 34: 18443–18451, 1988.*
Strockbine et al. Infect. Immun. 43: 1012–1018, 1984.*
Ito et al. Clin. Exp. Allergy 25: 522–528, 1995.*
Alber et al. J. Mol. Appl. Genetics 1: 419–434, 1982.*
Eroles et al., FEMS Microbiology Letters, vol. 128, pp. 95–100 (1995).
Maneu et al., Yeast Sequencing Reports, vol. 13, pp. 677–681 (1997).
Gil–Navarro et al., Journal of Bacteriology, vol. 179, No. 16, pp. 4992–4999 (1997).
Gomez et al., Infection and Immunity, vol. 64, No. 7, pp. 2577–2584 (1996).
Sepulveda et al., Infection and Immunity, vol. 63, No. 6, pp. 2173–2179 (1995).
Trinel et al., Infection and Immunity, vol. 61, No. 10, pp. 4398–4405 (1993).
Shen et al., Int. Arch. Allergy Appl. Immunol., vol. 96, No. 2, pp. 142–148 (1991).
Shen et al., Clinical and Experimental Allergy, vol. 21, No. 6, pp. 675–681 (1991).
Shoemaker, et al., cDNA Cloning and Functional Expression of the *Schistosoma mansonl* Protective Antigen Triose–Phosphate Isomerase, Proc. Natl. Acad. Sci. USA, Immunology, vol. 89, pp. 1842–1846, Mar. 1992.

* cited by examiner

*Primary Examiner*—S. Devi
(74) *Attorney, Agent, or Firm*—Birch, Stewart, Kolasch & Birch, LLP

(57) ABSTRACT

To provide a novel antigenic protein and a nucleic acid encoding the antigenic protein, which are useful for prophylaxis, treatment and diagnosis of diseases caused by fungi including *Candida albicans*. An antigenic protein characterized in that the antigenic protein is recognized by antiserum derived from a mammal having *Candida albicans*-infection resistance; and a nucleic acid encoding an antigenic protein which is recognized by antiserum derived from a mammal having *Candida albicans*-infection resistance.

15 Claims, 1 Drawing Sheet

SEQUENCE LISTING

<160> NUMBER OF SEQ ID NOS: 18

<210> SEQ ID NO 1
<211> LENGTH: 248
<212> TYPE: PRT
<213> ORGANISM: Candida albicans

<400> SEQUENCE: 1

```
Met Ala Arg Gln Phe Phe Val Gly Gly Asn Phe Lys Ala Asn Gly
 1               5                  10                  15

Thr Lys Gln Gln Ile Thr Ser Ile Ile Asp Asn Leu Asn Lys Ala
                20                  25                  30

Asp Leu Pro Lys Asp Val Glu Val Val Ile Cys Pro Pro Ala Leu
                35                  40                  45
```

-continued

```
Tyr Leu Gly Leu Ala Val Glu Gln Asn Lys Gln Pro Thr Val Ala
             50                  55                  60

Ile Gly Ala Gln Asn Val Phe Asp Lys Ser Cys Gly Ala Phe Thr
             65                  70                  75

Gly Glu Thr Cys Ala Ser Gln Ile Leu Asp Val Gly Ala Ser Trp
             80                  85                  90

Thr Leu Thr Gly His Ser Glu Arg Arg Thr Ile Ile Lys Glu Ser
             95                 100                 105

Asp Glu Phe Ile Ala Glu Lys Thr Lys Phe Ala Leu Asp Thr Gly
            110                 115                 120

Val Lys Val Ile Leu Cys Ile Gly Glu Thr Leu Glu Glu Arg Lys
            125                 130                 135

Gly Gly Val Thr Leu Asp Val Cys Ala Arg Gln Leu Asp Ala Val
            140                 145                 150

Ser Lys Ile Val Ser Asp Trp Ser Asn Ile Val Val Ala Tyr Glu
            155                 160                 165

Pro Val Trp Ala Ile Gly Thr Gly Leu Ala Ala Thr Pro Glu Asp
            170                 175                 180

Ala Glu Glu Thr His Lys Gly Ile Arg Ala His Leu Ala Lys Thr
            185                 190                 195

Ile Gly Ala Glu Gln Ala Glu Lys Thr Arg Ile Leu Tyr Gly Gly
            200                 205                 210

Ser Val Asn Gly Lys Asn Ala Lys Asp Phe Lys Asp Lys Ala Asn
            215                 220                 225

Val Asp Gly Phe Leu Val Gly Gly Ala Ser Leu Lys Pro Glu Phe
            230                 235                 240

Val Asp Ile Ile Lys Ser Arg Leu
            245

<210> SEQ ID NO 2
<211> LENGTH: 132
<212> TYPE: PRT
<213> ORGANISM: Candida albicans

<400> SEQUENCE: 2

Val Ala Glu Gln Val Gln Lys Thr Tyr Leu Asp Asp Val Thr Gly
  1               5                  10                  15

Glu Gln Val Ser Lys Thr Glu Leu Lys Lys Arg Gln Lys Gln Arg
             20                  25                  30

Ala Ile Glu Ala Lys Lys Ala Lys Ala Ala Ala Thr Pro Ala
             35                  40                  45

Lys Thr Thr Thr Lys Lys Lys Asp Glu Leu Ala Asp Leu Asn Pro
             50                  55                  60

Asn Gln Phe Phe Glu Ile Arg Ser Arg Gln Ile Ser Glu Leu Arg
             65                  70                  75

Glu Lys Asn Asn Ala Asp Pro Ser Ala Phe Asn Pro Tyr Pro His
             80                  85                  90

Lys Phe Asn Val Thr Thr Lys Ile Pro Glu Phe Val Glu Lys Tyr
             95                 100                 105

Ala His Leu Gln Arg Gly Glu Thr Leu Lys Asp Val Thr Val Ser
            110                 115                 120

Val Ser Gly Arg Ile Met Thr Lys Arg Glu Ser Gly
            125                 130
```

-continued

```
<210> SEQ ID NO 3
<211> LENGTH: 548
<212> TYPE: PRT
<213> ORGANISM: Candida albicans

<400> SEQUENCE: 3

Leu Lys Ser Lys Val Gly Ser Ile Phe Gly Arg Lys Lys Lys
  1               5                  10                  15

Glu Lys Phe Thr Gly Ala Asp Ser Ile Ala Glu Asp Glu Ser Leu
                 20                  25                  30

Ser Glu Val Ser Leu Pro Pro Thr Arg Thr Arg Asn Ser Ser Val
                 35                  40                  45

Leu Ser Arg Ser Asn Ser Thr Arg Arg Ser Phe Ile Asp Arg Phe
                 50                  55                  60

His Arg Asp Glu Ser Ser Thr Gly Ile Ser Arg Gln His Glu Gln
                 65                  70                  75

His Gln Gln Pro Leu Ser Asp Pro Leu Pro His Ala Glu Lys Pro
                 80                  85                  90

Gln Pro Glu Ile Pro Gln Ser Pro Glu Ala Pro Gln Ala Lys Ser
                 95                 100                 105

Leu Glu Pro Val Ser Glu Val Leu Lys Glu Leu Phe Pro Pro Met
                110                 115                 120

Gln Asn Gly Ser Glu Arg Lys Gly Glu Asn Gln Gln Ser Arg Val
                125                 130                 135

Asp Val Ser Ser Gln Thr Leu Ser Pro Val Thr Pro Thr His Asp
                140                 145                 150

Gly Phe Gly Gly Ser Val Lys Pro Leu Pro Glu Pro Val Asp Ser
                155                 160                 165

Pro Asn Val Ile Lys Tyr Asn Asp Ser Asp Ser Ser Thr Glu
                170                 175                 180

Glu Arg Arg Gly Ser Leu Leu Glu Lys His Asn Leu Glu Val Gln
                185                 190                 195

Pro Val Ser Ser Pro Phe Thr Thr Gln Pro Ala Pro Val Pro
                200                 205                 210

Gln Glu Ser Arg Ser Arg Gln Ser Ser Asp Gly Ile Tyr Ser Phe
                215                 220                 225

Glu Ala Gly Asp Asp Ser Asn Pro Ile Ser Ala Thr Pro Arg Ser
                230                 235                 240

Glu Gln Asn Val Phe Gly Gln Met Pro Asp Pro Asn Leu Ser Pro
                245                 250                 255

Glu Lys Thr Leu Ala Pro Pro Pro Pro Ser Arg Lys Val Leu
                260                 265                 270

His His Glu Glu Pro Thr Val Arg Asp Ser Ala Leu Phe His Asn
                275                 280                 285

Leu Pro Ala Ala Ser His Ser Gly Arg Asp Ser Val Met Ala Pro
                290                 295                 300

Leu Ala Ser Gln Asp Arg Gly His Ser Leu Leu Lys Asn Asp Phe
                305                 310                 315

Lys His Glu Asn Leu Ala Ser Thr Leu Gly Leu Ser Ser Ile
                320                 325                 330

Ala Glu Val Ile Asn Ala Ser Phe Lys Asp Gly Gln Leu Ile Lys
                335                 340                 345

Ser Gln Val Val Gly Glu Val Ala Phe Asn Tyr Asn Gly Asn Ala
                350                 355                 360
```

-continued

```
Ser Asp Pro Leu Val Val Thr Ile Pro Asn Ser Phe Asp Lys Val
                365                 370                 375

Leu Val Asn Lys Thr Phe Ile Glu Asp Leu Gly Gln Ser Lys Tyr
                380                 385                 390

Lys Val Asn Pro Thr Ser Ile Thr Ser Lys Thr Leu Gly Gly Leu
                395                 400                 405

Lys Tyr Leu Leu Lys Pro Thr Gln Val Pro Val Ile Ile Gln Gln
                410                 415                 420

Ile Trp Lys Phe Glu Pro His Gln Ser Ser Leu Met Val Ser Ile
                425                 430                 435

Arg Ser Thr Thr Pro Leu Val Leu Glu Asn Phe Val Val Ser Val
                440                 445                 450

Ala Leu Asn Gln Asp Ile Glu Ala Thr Ser Ala Ser Ser Lys Pro
                455                 460                 465

Gln Gly Ala Phe Asn Lys Glu Lys Asn Arg Ile Thr Trp Arg Tyr
                470                 475                 480

Pro Gln Ser Leu Ala Leu Asn Gly Val Glu Arg Leu Ile Ala Arg
                485                 490                 495

Phe Met Thr Asn Gly Leu Gly Ser Glu His Glu Ser Gly Val Gln
                500                 505                 510

Ile Lys Phe Gln Val Lys Asp Pro Gln Val Lys Tyr Cys Ser Ile
                515                 520                 525

Tyr Ser Glu Asn Gly Glu Ile Pro Thr Phe Arg Asn Leu Val
                530                 535                 540

Ser Gly Ser Tyr Ser Gly His Leu
                545

<210> SEQ ID NO 4
<211> LENGTH: 175
<212> TYPE: PRT
<213> ORGANISM: Candida albicans

<400> SEQUENCE: 4

Glu Glu Ile Pro Gln Gly Ala Asp Val Asn Val Ile Pro Lys Asn
  1               5                  10                  15

Glu Lys Lys Ala Arg Glu Leu Ile Lys Lys Leu Asn Leu Lys Gln
                 20                  25                  30

Ile Lys Gly Ile Ser Arg Val Thr Phe Lys Gln Arg Gly Asn Leu
                 35                  40                  45

Ile Tyr Ala Ile Asp Ser Pro Asp Val Tyr Arg Ser Ala Ala Gly
                 50                  55                  60

Thr Tyr Val Val Phe Gly Glu Ala Lys Val Asp Asp Met Asn Gln
                 65                  70                  75

Arg Ile Ala Glu Ala Gln Ala Gln Gln Ala Gln Gln Glu Ala Leu
                 80                  85                  90

Gln Lys Ala Ala Ala Asp Ala Gly Lys Thr Glu Asp Lys Ser Pro
                 95                 100                 105

Glu Ala Ile Thr Ala Asp Leu Glu Lys Ala Ser Leu Gly Asp Lys
                110                 115                 120

Lys Ala Glu Asp Glu Glu Asp Glu Gly Glu Ile Asp Glu Thr
                125                 130                 135

Gly Leu Asp Pro Lys Asp Ile Glu Ile Val Val Glu Gln Thr Gln
                140                 145                 150
```

-continued

```
Val Ser Arg Ala Lys Ala Val Lys Ala Leu Arg Asn His Asp Gly
            155                 160                 165

Asp Met Val Asn Ala Ile Met Asp Leu Ser
            170                 175

<210> SEQ ID NO 5
<211> LENGTH: 88
<212> TYPE: PRT
<213> ORGANISM: Candida albicans

<400> SEQUENCE: 5

Glu Asp Leu Phe Ala Leu Ser Lys Glu Thr Ala Gln Phe Glu Ala
  1               5                  10                  15

Asp Ser Phe Glu Leu Lys Gln Lys Leu Ala Val Ser His Glu Ala
             20                  25                  30

Lys Ser Val Leu Asp Ser Trp Val Arg Phe Glu Gln Gln Gln Arg
             35                  40                  45

Gln Leu Glu Gln Glu Gln Leu Ala Lys Glu Val Ile Asp Lys Val
             50                  55                  60

Asp Lys Glu Ile Ala Asn Pro Lys Phe Gln Asp Lys Val Leu Ala
             65                  70                  75

Glu Ser Leu Asn Glu Ile Glu Lys Leu Phe Ala Lys Asn
             80                  85

<210> SEQ ID NO 6
<211> LENGTH: 264
<212> TYPE: PRT
<213> ORGANISM: Candida albicans

<400> SEQUENCE: 6

Met Pro Ala Ser Arg Glu Asp Ser Val Tyr Leu Ala Lys Leu Ala
  1               5                  10                  15

Glu Gln Ala Glu Arg Tyr Glu Glu Met Val Glu Asn Met Lys Ala
             20                  25                  30

Val Ala Ser Ser Gly Gln Glu Leu Ser Val Glu Glu Arg Asn Leu
             35                  40                  45

Leu Ser Val Ala Tyr Lys Asn Val Ile Gly Ala Arg Arg Ala Ser
             50                  55                  60

Trp Arg Ile Val Ser Ser Ile Glu Gln Lys Glu Glu Ala Lys Gly
             65                  70                  75

Asn Glu Ser Gln Val Ala Leu Ile Arg Asp Tyr Arg Ala Lys Ile
             80                  85                  90

Glu Ala Glu Leu Ser Lys Ile Cys Glu Asp Ile Leu Ser Val Leu
             95                 100                 105

Ser Asp His Leu Ile Thr Ser Ala Gln Thr Gly Glu Ser Lys Val
            110                 115                 120

Phe Tyr Tyr Lys Met Lys Gly Asp Tyr His Arg Tyr Leu Ala Glu
            125                 130                 135

Phe Ala Ile Ala Glu Lys Arg Lys Glu Ala Ala Asp Leu Ser Leu
            140                 145                 150

Glu Ala Tyr Lys Ala Ala Ser Asp Val Ala Val Thr Glu Leu Pro
            155                 160                 165

Pro Thr His Pro Ile Arg Leu Gly Leu Ala Leu Asn Phe Ser Val
            170                 175                 180

Phe Tyr Tyr Glu Ile Leu Asn Ser Pro Asp Arg Ala Cys His Leu
            185                 190                 195
```

-continued

Ala Lys Gln Ala Phe Asp Asp Val Ala Asp Leu Glu Thr Leu
               200                 205                 210

Ser Glu Asp Ser Tyr Lys Asp Ser Thr Leu Ile Met Gln Leu Leu
               215                 220                 225

Arg Asp Asn Leu Thr Leu Trp Thr Asp Leu Ser Glu Ala Pro Ala
               230                 235                 240

Ala Thr Glu Glu Gln Gln Ser Ser Gln Ala Pro Ala Ala Gln
               245                 250                 255

Pro Thr Glu Gly Lys Ala Asp Gln Glu
               260

<210> SEQ ID NO 7
<211> LENGTH: 224
<212> TYPE: PRT
<213> ORGANISM: Candida albicans

<400> SEQUENCE: 7

Gln Lys Thr Ala Glu Glu Arg Ala Ala Ala Lys Lys Val Arg Lys
  1               5                  10                  15

Ala Ala Asn Lys Glu Lys Arg Lys Val Ile Phe Asp Arg Ala Ala
                 20                  25                  30

Ala Tyr Gln Lys Glu Tyr Thr Glu Ala Glu Arg Ser Val Ile Lys
                 35                  40                  45

Ala Lys Arg Asp Ala Lys Ala Ser Asn Ser Tyr Tyr Val Asp Ala
                 50                  55                  60

Gln Pro Lys Leu Val Phe Val Arg Ile Lys Gly Ile Asn Lys
                 65                  70                  75

Ile Pro Pro Lys Pro Arg Lys Val Leu Gln Leu Leu Arg Leu Thr
                 80                  85                  90

Gln Ile Asn Ala Gly Val Phe Val Arg Leu Thr Lys Ala Thr Ser
                 95                 100                 105

Glu Leu Ile Lys Leu Ala Glu Pro Tyr Val Ala Tyr Gly Tyr Pro
                110                 115                 120

Ser Leu Ser Thr Ile Arg Gln Leu Val Tyr Lys Arg Gly Phe Gly
                125                 130                 135

Lys Val Asn Lys Gln Arg Ile Ala Leu Ser Asp Asn Ala Ile Ile
                140                 145                 150

Glu Ala Asn Leu Gly Lys Phe Asn Ile Leu Ser Ile Glu Asp Leu
                155                 160                 165

Ile His Glu Ile Tyr Thr Val Gly Pro Asn Phe Lys Gln Val Ser
                170                 175                 180

Asn Phe Leu Trp Pro Phe Lys Leu Ser Asn Pro Asn Gly Gly Phe
                185                 190                 195

Arg Ala Arg Lys Phe Gln His Phe Ile Gln Gly Gly Asp Thr Gly
                200                 205                 210

Asn Arg Glu Gln Phe Ile Asn Ala Leu Val Lys Gln Met Asn
                215                 220

<210> SEQ ID NO 8
<211> LENGTH: 115
<212> TYPE: PRT
<213> ORGANISM: Candida albicans

<400> SEQUENCE: 8

Lys Lys Leu Ala His Ala Glu Met Glu Gln Ala Ala Glu Leu Leu
  1               5                  10                  15

-continued

```
Ala Glu Glu Ala Lys Thr Thr Lys Ser Ala Ala Ala Arg Thr
             20                  25                  30

Ala Ala Ser Gly Val Thr Thr Ala Ser Ala Gln Asn Ala Lys Thr
         35                  40                  45

Ile Arg Ser Pro Ile Val Gln Ala Val Arg Thr Leu Trp Lys Gln
         50                  55                  60

Gly Gly Ile Lys Ala Phe Tyr Val Gly Asn Gly Leu Asn Val Met
             65                  70                  75

Lys Val Phe Pro Glu Ser Ala Met Lys Phe Gly Ser Phe Glu Ala
             80                  85                  90

Ala Lys Arg Phe Phe Ala Arg Ile Glu Gly Val Asn Asp Thr Thr
             95                 100                 105

Lys Ile Ser Lys Ile Ser Thr Tyr Leu Ala
            110                 115

<210> SEQ ID NO 9
<211> LENGTH: 613
<212> TYPE: PRT
<213> ORGANISM: Candida albicans

<400> SEQUENCE: 9

Met Ala Asp Gly Val Phe Gln Gly Ala Ile Gly Ile Asp Leu Gly
 1               5                  10                  15

Thr Thr Tyr Ser Cys Val Ala Thr Tyr Asp Ser Ala Val Glu Ile
             20                  25                  30

Ile Ala Asn Glu Gln Gly Asn Arg Val Thr Pro Ser Phe Val Ala
         35                  40                  45

Phe Thr Ser Glu Glu Arg Leu Ile Gly Asp Ala Ala Lys Asn Gln
         50                  55                  60

Ala Ala Leu Asn Pro Lys Asn Thr Val Phe Asp Ala Lys Arg Leu
             65                  70                  75

Ile Gly Arg Ala Phe Asp Asp Glu Ser Val Gln Lys Asp Ile Lys
             80                  85                  90

Ser Trp Pro Phe Lys Val Val Glu Ser Asn Gly Gln Pro Leu Ile
             95                 100                 105

Glu Val Glu Tyr Leu Asp Glu Thr Lys Thr Phe Ser Pro Gln Glu
            110                 115                 120

Ile Ser Ser Met Val Leu Thr Lys Met Lys Glu Ile Ala Glu Ala
            125                 130                 135

Lys Ile Gly Lys Lys Val Glu Lys Ala Val Thr Val Pro Ala
            140                 145                 150

Tyr Phe Asn Asp Ala Gln Arg Gln Ala Thr Lys Asp Ala Gly Ala
            155                 160                 165

Ile Ala Gly Leu Asn Val Leu Arg Ile Ile Asn Glu Pro Thr Ala
            170                 175                 180

Ala Ala Ile Ala Tyr Gly Leu Gly Ala Gly Lys Ser Glu Lys Glu
            185                 190                 195

Arg His Val Leu Ile Phe Asp Leu Gly Gly Gly Thr Phe Asp Val
            200                 205                 210

Ser Leu Leu Asn Ile Thr Gly Gly Val Phe Thr Val Lys Ala Thr
            215                 220                 225

Ala Gly Asp Thr His Leu Gly Gly Gln Asp Phe Asp Thr Asn Leu
            230                 235                 240

Leu Glu His Phe Lys Lys Glu Phe Gln Lys Lys Thr Gly Asn Asp
            245                 250                 255
```

```
Ile Ser Ser Asp Ala Arg Ala Leu Arg Arg Leu Arg Thr Ala Cys
            260                 265                 270

Glu Arg Ala Lys Arg Ser Leu Ser Ser Gly Thr Gln Thr Thr Val
            275                 280                 285

Glu Ile Asp Ser Leu Phe Asp Gly Glu Asp Phe Ser Ala Asn Ile
            290                 295                 300

Thr Arg Ala Arg Phe Glu Asp Ile Asn Ser Ala Leu Phe Lys Ser
            305                 310                 315

Thr Leu Glu Pro Val Glu Gln Val Leu Lys Asp Ala Lys Ile Ser
            320                 325                 330

Lys Ser Gln Val Asp Glu Val Leu Val Gly Gly Ser Thr Arg
            335                 340                 345

Ile Pro Lys Val Gln Lys Leu Leu Ser Asp Phe Phe Asp Gly Lys
            350                 355                 360

Gln Leu Glu Lys Ser Ile Asn Pro Asp Glu Ala Val Ala Tyr Gly
            365                 370                 375

Ala Ala Val Gln Gly Ala Ile Leu Thr Gly Gln Ser Thr Asn Asp
            380                 385                 390

Asp Thr Lys Asp Leu Leu Leu Leu Asp Val Ile Pro Leu Ser Leu
            395                 400                 405

Gly Val Ala Met Gln Gly Asn Val Phe Ala Pro Val Val Pro Arg
            410                 415                 420

Asn Thr Thr Val Pro Thr Ile Lys Arg Arg Thr Phe Thr Thr Val
            425                 430                 435

Ala Asp His Gln Thr Thr Val Gln Phe Pro Val Tyr Gln Gly Glu
            440                 445                 450

Arg Val Asn Cys Ser Glu Asn Thr Leu Leu Gly Glu Phe Asp Leu
            455                 460                 465

Lys Asn Ile Pro Pro Met Gln Ala Gly Glu Pro Val Leu Glu Ala
            470                 475                 480

Ile Phe Glu Val Asp Ala Asn Gly Ile Leu Lys Val Thr Ala Val
            485                 490                 495

Glu Lys Ser Thr Gly Arg Ser Ala Asn Ile Thr Ile Ser Asn Ser
            500                 505                 510

Ile Gly Arg Leu Ser Thr Glu Glu Ile Glu Lys Met Ile Ser Asp
            515                 520                 525

Ala Glu Lys Phe Lys Ser Ser Asp Asp Ala Phe Ala Lys Arg His
            530                 535                 540

Glu Gln Lys Gln Lys Leu Glu Ala Tyr Val Ala Ser Val Glu Ser
            545                 550                 555

Thr Val Thr Asp Pro Val Leu Ser Ala Lys Leu Lys Lys Ser Ala
            560                 565                 570

Lys Asp Lys Ile Glu Ala Ala Leu Ser Asp Ala Leu Gln Thr Leu
            575                 580                 585

Glu Ile Glu Glu Ser Ser Ala Asp Asp Tyr Arg Lys Ala Glu Leu
            590                 595                 600

Ala Leu Lys Arg Ala Val Thr Lys Gly Met Ala Thr Arg
            605                 610

<210> SEQ ID NO 10
<211> LENGTH: 837
<212> TYPE: DNA
<213> ORGANISM: Candida albicans
```

-continued

<400> SEQUENCE: 10

```
agcacaatgg ctcgtcaatt tttcgtaggt ggtaacttca aagctaacgg taccaaacaa      60
caaatcactt caatcatcga caacttgaac aaggctgatt taccaaagga tgtcgaagtt     120
gtcatttgtc cacccgccct ttaccttggt ttagctgttg agcaaaacaa acaaccaact     180
gttgccattg gtgctcaaaa tgttttgac aagtcatgtg gtgctttcac tggtgaaacc     240
tgtgcttctc aaatcttgga tgttggtgcc agctggactt taactggtca cagtgaaaga     300
agaaccatta tcaaagaatc cgatgaattc attgctgaaa aaaccaagtt tgccttggac     360
actggtgtca agttattttt atgtattggt gaaaccttag aggaaagaaa aggtggtgtc     420
actttggatg tttgtgccag acaattggat gctgtttcca agattgtttc tgattggtca     480
aacattgttg ttgcttacga acctgtttgg gcaattggta ctggtttagc cgctacccca     540
gaagatgctg aagaaaccca caaggtatt agagctcatt tggccaagac cattggtgcc     600
gaacaagctg aaaaaccag aatcttgtac ggtggttcag ttaacggtaa gaacgctaag     660
gatttcaaag acaaagcaaa tgttgatggt ttcttagtcg gtggtgcttc attaaaacca     720
gaatttgttg atatcatcaa atctagatta taaacagtat attaaaaact atatgcctat     780
agaatttagc atgttgttgt gaatttgtaa tgaatctata aaaatgtgct catgaaa         837
```

<210> SEQ ID NO 11
<211> LENGTH: 396
<212> TYPE: DNA
<213> ORGANISM: Candida albicans

<400> SEQUENCE: 11

```
gttgccgaac aagttcaaaa aacctatttg gacgatgtca ccggtgaaca agtttccaaa      60
accgaattga aaaaaagaca aaaacaaaga gcaattgaag ctaagaaagc tgctaaagct     120
gctgccactc cagccaaaac taccaccaaa aagaaagatg aattggctga tttgaatcca     180
aatcaatttt tcgaaatcag atctcgtcaa atttctgaat taagagagaa aaacaatgct     240
gatccatcag ctttcaaccc ataccctcac aaattcaatg ttaccaccaa aattcccgaa     300
tttgttgaaa atacgcccca tttgcaaaga ggggaaactt tgaaagatgt caccgtttcc     360
gttagtggta gaataatgac caaaagagaa tcagga                                396
```

<210> SEQ ID NO 12
<211> LENGTH: 1700
<212> TYPE: DNA
<213> ORGANISM: Candida albicans

<400> SEQUENCE: 12

```
ctaaagtcca aagttggttc aattttttggc agaaaaaaga agaaggaaaa attcactgga      60
gctgattcaa ttgctgaaga tgaatcatta tctgaggttt ctttgccacc tacaagaact     120
aggaattcat cggtgttgtc tcgcagtaac tcaactagaa gatctttat tgaccgcttc     180
catagagatg agtctagcac tggcattagc agacaacatg agcagcacca gcagcctttg     240
agtgatcctt tgcctcacgc agagaagcct caaccgaaaa ttccccaatc accagaagct     300
ccacaggcca aatcactaga gcctgtatca gaagtactaa agaactgtt cccacctatg     360
caaaacgggt ccgaaggaa aggtgaaaat cagcagtcga gagttgatgt atcctctcaa     420
accttgtcac cagttactcc tactcacgat ggatttggtg gttctgttaa accattacca     480
gaacctgttg attctccaaa tgtgattaaa tacaatgact cggacgactc ttctacagaa     540
gaacgtagag gctcgttact tgaaaaacac aatttagaag tacaacctgt atcttcccca     600
```

-continued

| | |
|---|---|
| ttcactactc aaccgccagc acctgtgcca caagaatcca gatctagaca aagcagtgat | 660 |
| ggcatttact cgtttgaagc gggtgatgat tccaacccaa tctcggctac tccaagatcc | 720 |
| gagcaaaatg tgtttggaca gatgccagac ccaaatttgt ctcctgaaaa gactcttgct | 780 |
| ccaccaccac caccttcgag aaaagttttg caccatgaag aaccaactgt aagggattca | 840 |
| gctcttttcc acaatttacc tgctgcctcc cattctggaa gagattcggt aatggctcca | 900 |
| ttagcaagtc aagacagggg tcattcgttg ttgaaaaatg atttcaaaca cgaaaacttg | 960 |
| gcatccaccc tcggattgag ctcttctatt gctgaagtca tcaatgccag ctttaaggat | 1020 |
| ggacagttga ttaaatcaca agtagttggt gaagtggcct tcaattataa tggtaatgct | 1080 |
| tccgatccac ttgtggtcac tattcctaat agtttcgata agtactcgt gaacaagact | 1140 |
| tttattgagg atttaggtca aagcaagtat aaagtgaacc caacttcaat tacgtctaaa | 1200 |
| actcttggtg ggttgaaata tcttttgaaa ccaacacagg taccagtgat aattcaacaa | 1260 |
| atatggaaat ttgaacctca tcagtcaagt ttgatggtta gcattcgttc aactacacct | 1320 |
| ttggtattgg aaaattttgt tgtctctgta gctttgaatc aagacattga agcaacatct | 1380 |
| gcttcctcaa agcctcaagg tgcgtttaat aaagagaaaa acagaataac atggagatat | 1440 |
| ccacagtccc tcgcattgaa tggtgtagag cgtttgatag ctagatttat gactaatgga | 1500 |
| ttgggttccg aacatgagtc tggtgtgcag attaaatttc aagttaagga tccacaagtc | 1560 |
| aagtactgta gtatttacag tgagaatggc aagagattc ctacgtttag aaatttggtt | 1620 |
| agcggtagtt atagtggtca tctttaagtt atctgttttg agattagtct cttgttgaat | 1680 |
| tgaaaaaaaa aaaaacgtga | 1700 |

<210> SEQ ID NO 13
<211> LENGTH: 585
<212> TYPE: DNA
<213> ORGANISM: Candida albicans

<400> SEQUENCE: 13

| | |
|---|---|
| gaagaaatcc cacaaggtgc tgacgttaat gtcattccaa aaaacgaaaa gaaagctaga | 60 |
| gaattgatca agaagttaaa cttgaaacaa atcaaaggta tttccagagt cactttcaaa | 120 |
| caaagaggaa acttgattta tgccattgat tccccggatg tctacagatc tgctgctggt | 180 |
| acttatgttg tctttggtga agctaaagtt gatgacatga ccaaagaat tgctgaagct | 240 |
| caagctcaac aagctcaaca agaagcttta caaaaagctg ctgctgatgc cggtaaaacc | 300 |
| gaagacaaat caccagaagc tattactgct gatttagaaa aggcttcttt gggtgacaag | 360 |
| aaagctgaag acgaagaaga agacgaaggt gagattgacg aaactggttt ggatccaaaa | 420 |
| gatattgaaa ttgttgttga acaaacccaa gtttctagag ccaaggctgt caaggcttta | 480 |
| agaaatcacg acggtgacat ggtcaacgct attatggatt tgtcttagat aatacgtgtg | 540 |
| tatattgact agctaatata atatatgtat atatttatct gtaaa | 585 |

<210> SEQ ID NO 14
<211> LENGTH: 352
<212> TYPE: DNA
<213> ORGANISM: Candida albicans

<400> SEQUENCE: 14

| | |
|---|---|
| gaagatttgt ttgctttatc taaagaaacc gctcaattcg aagctgattc atttgaatta | 60 |
| aaacaaaaat tggctgtttc tcacgaagct aaatctgttt tggactcttg ggttagattt | 120 |
| gaacaacaac aaagacaatt ggaacaagaa caattggcca aagaagtcat tgataaagtt | 180 |

```
gacaaagaaa ttgctaatcc aaaattccaa gacaaagtat tggctgaatc tcttaacgaa      240
atcgaaaaat tgtttgctaa aaactagata gattttttat atatataacg aacaaaaagg      300
tttgatgcct aaaggagtgt cactcaaata tatatttcat atattattta aa              352

<210> SEQ ID NO 15
<211> LENGTH: 880
<212> TYPE: DNA
<213> ORGANISM: Candida albicans

<400> SEQUENCE: 15
aaaagaacaa aaattataat gccagcctcc cgtgaagatt ccgtttacct tgctaaatta       60
gccgaacaag cagaacgtta tgaagaaatg gttgaaaaca tgaaagccgt tgcttcctct      120
ggccaagaat tgtctgttga agaacgtaat ttattatctg ttgcttacaa gaatgtcatt      180
ggtgctcgtc gtgcttcttg gagaattgtt tcatcaattg aacaaaaaga agaagccaaa      240
ggaaatgaga gccaagttgc tttgatcaga gattaccgtg ccaagattga agctgaattg      300
tctaaaattt gtgaagatat tctctctgtg ttgagcgacc atttaattac atctgcccaa      360
actggtgaat caaagtatt ttactacaag atgaaaggtg attaccacag atacttggct       420
gaatttgcta tcgctgaaaa acgtaaggaa gctgctgatt tatcattaga ggcttataaa      480
gctgcttctg acgttgctgt gaccgagttg ccaccaaccc atccaatcag attaggttta      540
gcattgaact tctctgtttt ctactatgaa attttgaact ccccagatag agcttgtcat      600
ttagctaaac aagctttcga tgatgctgtt gctgatttag aaaccttatc tgaagattca      660
tacaaggatt caactttgat tatgcaatta ttgagagata acttgacttt atggaccgat      720
ttatctgaag ccccagctgc cactgaagaa caacaacaat ccagtcaagc tccagctgct      780
caaccaacag aaggtaaggc tgatcaagaa tagattgtat gtaaagtttt agttatattt      840
cttgtgtgaa tttaatttag tttattgtat tgtattcaaa                            880

<210> SEQ ID NO 16
<211> LENGTH: 721
<212> TYPE: DNA
<213> ORGANISM: Candida albicans

<400> SEQUENCE: 16
caaaaaactg ctgaagaaag agctgctgcc aagaaggtca gaaaagctgc caacaaagaa       60
aagagaaagg ttatctttga cagagctgct gcttaccaaa aggaatacac tgaagctgaa      120
agatctgtca tcaaagccaa gagagatgct aaagcttcta actcttacta cgttgatgct      180
caaccaaaat tggttttcgt tgtcagaatc aagggtatta acaagattcc accaaagcca      240
agaaaggtct tgcaattatt aagattgacc caaatcaatg ctggtgtttt cgtcagattg      300
actaaagcca cctctgaatt gatcaaattg gctgaaccat acgttgctta cggttaccca      360
tctttgtcta ccatcagaca attagtttac aagagaggtt tcggtaaggt caacaagcaa      420
agaattgctt tgtccgacaa tgccatcatt gaagccaact tgggtaaatt caatatcttg      480
tctattgaag atttgattca cgaaatttac actgttggtc caaacttcaa acaagtcagc      540
aacttcttgt ggccattcaa attatccaat ccaaacggtg gtttcagagc cagaaaattc      600 caacactttta tccaaggtgg tgacaccggt aacagagaac aattcattaa cgctttggtc      660
aaacaaatga actaagttta atgtatcatt tcaaacttac cttatctacc tactacacct      720
c                                                                      721
```

```
<210> SEQ ID NO 17
<211> LENGTH: 345
<212> TYPE: DNA
<213> ORGANISM: Candida albicans

<400> SEQUENCE: 17
aaaaaattag cacatgcaga aatggaacag gcagcagaac tactagcaga agaagccaaa      60
accaccaaga gcgccgctgc agcaagaaca gcagcatctg gtgtaacaac tgcatcagct     120
caaaatgcaa agaccattag atcacccata gttcaagcag taagaacact ttggaaacaa     180
ggaggaatta aagcatttta cgttggtaat ggattaaatg taatgaaagt gtttcctgaa     240
tcagcaatga aatttggctc ttttgaagct gccaaacgat tttttgctcg aattgaaggt     300
gttaatgaca ccaccaaaat ctccaaaatc tctacatatt tagcc                    345

<210> SEQ ID NO 18
<211> LENGTH: 1026
<212> TYPE: DNA
<213> ORGANISM: Candida albicans

<400> SEQUENCE: 18
gttgaacaag ttttgaaaga tgctaaaatc agcaaatccc aagttgacga agttgtcttg      60
gttggtggtt ccaccagaat tccaaaagtc caaaaattgt tgtctgactt ctttgacggt     120
aaacaattgg aaaaatctat taacccagat gaagctgttg cttacggtgc tgctgttcaa     180
ggtgctatct tgaccggtca atccactaac gatgacacca aagacttgtt attgttggat     240
gtcattccat tgtctctcgg tgttgctatg caaggtaacg ttttttgcccc agttgtccca     300 agaaacacca ctgttccaac catcaagaga agaactttca ccactgttgc tgaccaccaa     360
accactgttc aattcccagt ttaccaaggt gaacgtgtca actgtactga aaacaccttg     420
ttgggtgaat ttgacttgaa aaacatccca ccaatgcaag ccggtgaacc agttttggaa     480 gccattttg aagttgatgc taacggtatc ttgaaggtca ctgctgttga aaaatccact     540
ggtagatctg ctaacatcac catctccaac tccattggta gattgtcaac tgaagaaatc     600
gaaaaaatga tctctgatgc tgaaaaattc aaatcatccg atgatgcttt cgccaagaga     660
cacgaacaaa aacaaaaatt agaagcttac gttgcttccg ttgaatctac tgtcactgac     720
ccagtcttgt ctgctaaatt gaagaaatct gccaaggaca agatcgaagc tgctttgtct     780
gatgctttgc aaactttgga aattgaagaa tcttctgctg acgactacag aaaagctgaa     840
ttagctttga agagagctgt caccaaaggt atggctaccc gttaagtaaa ctagatgttg     900
aatgtcattt gttttacgcc atatttttt tttcccttta acatcattca cccctccccc     960
ttactatgtg tgtatattta gtatagtcat ccactaatac agaaagtaaa aataaatttg    1020
attaaa                                                                1026
```

ANTIGEN PROTEIN AND NUCLEIC ACID CODING FOR SAID PROTEIN

This application is the national phase under 35 U.S.C. §371 of PCT International Application No. PCT/JP98/04326 which has an International filing date of Sep. 28, 1998, which designated the United States of America.

TECHNICAL FIELD

The present invention relates to *Candida albicans* antigenic protein, and a nucleic acid encoding thereof, which are useful for prophylaxis, treatment and diagnosis of fungal infectious disease or allergosis. The present invention further relates to a vector comprising the nucleic acid, and a transformant resulting from transformation with the vector. The present invention further relates to a method for producing the antigenic protein of the present invention, wherein the method comprises culturing the above transformant. The present invention further relates to a pharmaceutical composition or diagnostic composition, each comprising the antigenic protein or nucleic acid of the present invention.

BACKGROUND ART

Although *Candida albicans* normally colonizes in the human body, normal individuals are usually resistant to infection therewith and seldom suffer from systemic infectious disease caused thereby. Even in normal individuals, however, this fungus can cause local infectious disease; in females, particularly in pregnant women, it can cause vaginal candidiasis. On the other hand, in humans rendered immunocompromised as a result of administration of an anticancer agent for treatment of a cancer, such as leukemia, administration of an immunosuppressant for organ transplantation, infection with AIDS, or the like, this fungus can cause systemic infectious diseases affecting various internal organs. Furthermore, this fungus represents the most common fungal allergen as a cause of allergosis. In addition, most humans are immunologically sensitized with the normally colonizing fungus *Candida albicans*, possess antibodies against its components, and have acquired cellular immunity thereto.

Many of the *Candida albicans* antigens are cell wall components on the cell surface, mainly polysaccharides, such as mannan and glucan, mannan and its conjugate with protein being particularly predominant. In addition, in sera from patients with *Candida albicans* infection or those with allergy, antibodies against the intracellular components enolase, HSP90 (heat shock protein 90), phosphoglycerate kinase, or alcohol dehydrogenase are detected, in addition to the antibodies against the aforementioned cell wall components.

Fungi of the genus *Candida* other than *Candida albicans*, for instance, *C. tropicalis* and *C. glabrata*, cause infectious disease mainly in immunocompromised hosts. Fungi other than those of the genus *Candida*, for instance, fungi of the genera *Aspergillus, Penicillium*, and *Alternaria*, also occur widely in our environment and are very close to mammals, including humans. Although these fungi are yeast-like or mycelial in the cellular morphology to grow, their cellular structures are basically similar to each other, all having a surface layer surrounded by a thick cell wall. Although the chemical structure of the cell wall varies to some extent depending on kind of fungus, the cell wall components mainly comprise polysaccharides, such as mannan, glucan, and chitin. In addition, the proteins and other components in the cell membrane and cytoplasm surrounded by the cell wall are also basically similar to each other. Many of these fungi also cause infectious disease in immunocompromised hosts, or serve as causes of allergy.

As pathogenic factors and allergens in fungus-involved disease, some antigen molecules derived from fungus have been isolated and identified. Isolation and identification of these antigen molecules are usually achieved using sera from fungus-sensitized mammals; the most common of such antigen molecules that have been identified so far are the cell wall components surrounding the fungal surface layer. In addition to the above components, a number of antigen molecules have been isolated and identified, and are under investigation for the purposes of diagnosis and therapy. It should be noted, however, that not all antigens reactive to antibodies retained in fungus-sensitized state act effectively in infectious disease or allergosis.

An object of the present invention is to provide a novel antigenic protein useful in the treatment and diagnosis of diseases caused by fungi including *Candida albicans*. Another object of the present invention is to provide a nucleic acid encoding the antigenic protein. Still another object of the present invention is to provide a vector comprising the nucleic acid, and a transformant resulting from transformation with the vector. Still another object of the present invention is to provide a method for producing the antigenic protein of the present invention, wherein the method comprises culturing the transformant. A further object of the present invention is to provide a pharmaceutical composition and diagnostic composition, each comprising the antigenic protein or nucleic acid of the present invention.

DISCLOSURE OF INVENTION

The present inventors have investigated about a method for conferring *Candida albicans*-infection resistance to mammals, such as mice and rats, which are sensitive to *Candida albicans* infection. As a result, the present inventors have clarified that such mammals can acquire strong resistance to infection by immunizing the mammals with *Candida albicans* cells as the antigen in mixture with an adjuvant of incomplete Freund's adjuvant. The present inventors have also clarified that CD4-positive T-cells play a key role in the infection resistance. Furthermore, antisera derived from the above immunologically sensitized mammals acquiring the infection resistance have unexpectedly lower antibody titers against the cell wall-derived components in the fungal cell surface layer, and higher antibody titers against the components derived from protoplast cells of fungi deprived of cell wall, in comparison with, for example, Factor Serum No. 1 (manufactured by IATRON LABORATORIES, INC.), a commercially available anti-*Candida* serum.

Having assumed that the serum from an immunologically sensitized mammal showing the above infection resistance is richer in antibodies acting effectively against fungal infectious disease, and remarked on the antibodies contained in the serum, the present inventors have screened for antigenic proteins recognized by the antisera. Concretely, an expression library was prepared on the basis of *Candida albicans* cDNA and screened by immunoscreening for such antigenic proteins. As a result, the present inventors have found eight kinds of antigenic proteins as recombinant *Escherichia coli* proteins, isolated their DNA, determined the nucleotide sequences, and at the same time determined the amino acid sequences from the nucleotide sequences. The present invention has been accomplished thereby.

Concretely, the gist of the present invention relates to:

an antigenic protein characterized in that the antigenic protein is recognized by antiserum derived from a mammal having *Candida albicans*-infection resistance;

an antigenic protein immunologically equivalent to the antigenic protein according to item [1] above;

a nucleic acid encoding an antigenic protein which is recognized by antiserum derived from a mammal having *Candida albicans*-infection resistance;

a vector comprising the nucleic acid according to item [3] above;

a transformant resulting from transformation with the vector according to item [4] above;

a method for producing an antigenic protein which is recognized by antiserum derived from a mammal having *Candida albicans*-infection resistance, characterized in that the method comprises culturing the transformant according to item [5] above under conditions capable of expressing an antigenic protein encoded by the nucleic acid according to item [3] above;

a pharmaceutical composition characterized in that the pharmaceutical composition comprises the antigenic protein according to item [1] or [2] above, or an antigenic protein obtainable by the method according to item [6] above;

a diagnostic composition characterized in that the diagnostic composition comprises the antigenic protein according to item [1] or [2] above, or an antigenic protein obtainable by the method according to item [6] above;

a pharmaceutical composition characterized in that the pharmaceutical composition comprises the nucleic acid according to item [3] above;

a diagnostic composition characterized in that the diagnostic composition comprises the nucleic acid according to item [3] above.

an antibody capable of specifically binding to the antigenic protein according to item [1] or [2] above, or a fragment thereof; and a nucleic acid capable of specifically binding to the nucleic acid according to item [3] above.

Figure 1:
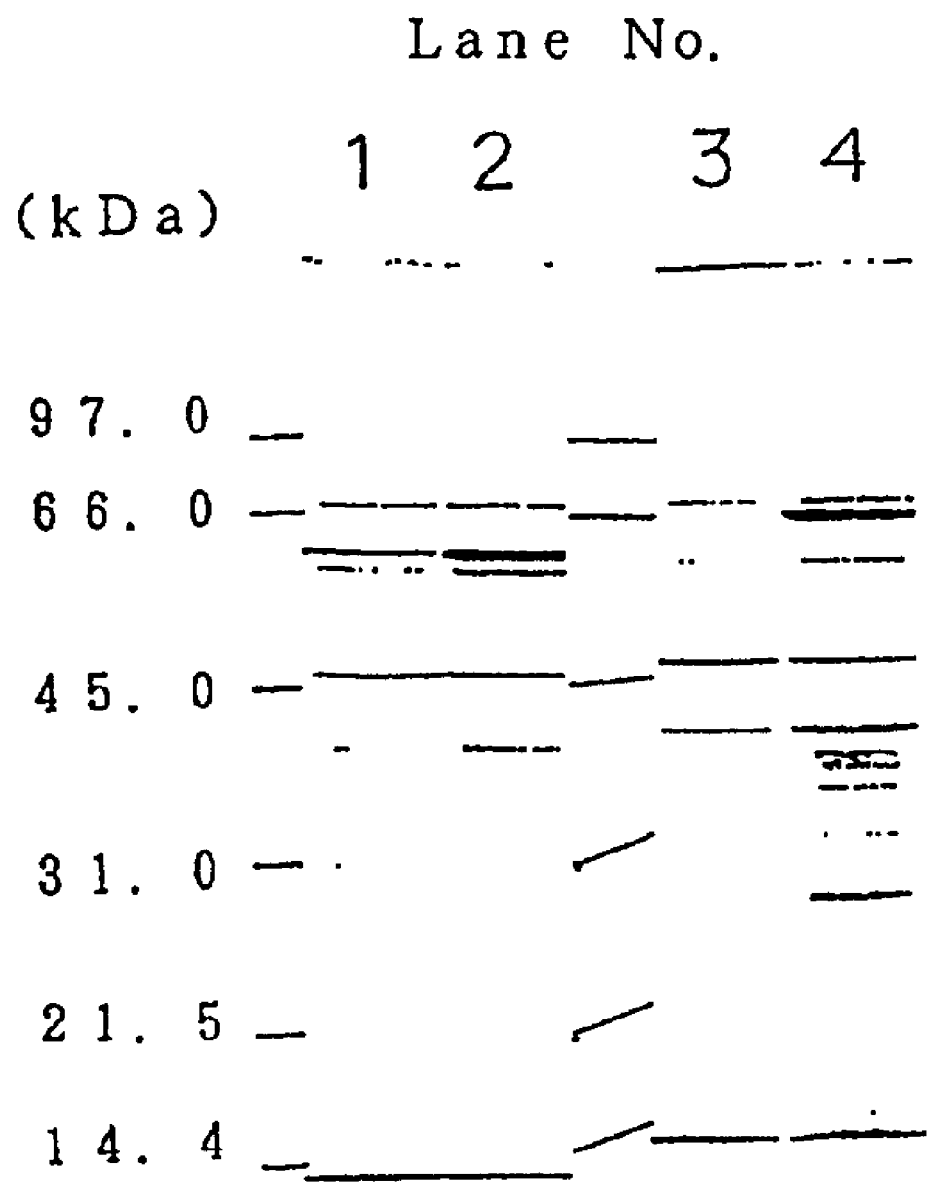
FIG. 1 shows analytical results of SDS-polyacrylamide gel electrophoresis of recombinant proteins each derived from lysyl tRNA synthethase homologue genes and TPI (triose phosphate isomerase) homologue genes of *C. albicans*.

The sample of lane 1 in FIG. 1 is a polypeptide obtained before the induction of expression of the transformant in which the lysyl-tRNA synthase homologue gene (before addition of IPTG) was transduced; and the sample of lane 2 is a polypeptide obtained after the induction (after addition of IPTG). The sample of lane 3 comprises the polypeptide obtained before the induction of expression of the transformant in which the TPI homologue gene was transduced, and the sample of lane 4 is the polypeptide obtained after the induction.

BEST MODE FOR CARRYING OUT THE INVENTION

1. Antigenic Proteins of Present Invention

The antigenic protein of the present invention is a protein recognized by antiserum derived from a mammal having *Candida albicans*-infection resistance.

In the present specification, the term "mammal having *Candida albicans*-infection resistance" refers to a mammal allowed to acquire infection resistance by immunization with antigens derived from *Candida albicans*, the mammal being alive even when *Candida albicans* cells at a lethal number before immunization are administered (dead cell counts within 10 days after intravenous infection).

Such a mammal can, for example, be obtained in the manner described below.

At least two subcutaneous or intraperitoneal administrations are given at an interval of 1 to 2 weeks, of a mixture of live *Candida albicans* cells as the antigen and incomplete Freund's adjuvant (IFA) for strong induction of cellular immunity to an animal sensitive to *Candida albicans* infection, including, for instance, a mouse such as C57BL/6, BALB/c, or DBA/2, a rat such as Sprague-Dawley or Wistar, etc., thereby immunizing the animal. The animal which has acquired infection resistance is used as a mammal having *Candida albicans*-infection resistance.

In the present specification, the term "antiserum derived from a mammal having *Candida albicans*-infection resistance" refers to an antiserum obtained from a mammal having *Candida albicans*-infection resistance.

As the above antiserum, there can be used, for example, those obtained by collecting blood from a mammal having *Candida albicans*-infection resistance at 1 to 2 weeks after final immunization. Such antiserum is an antiserum obtained after 1 week to 1 month following at least two immunizations at an interval of about 1 week, wherein preferably a mouse, more preferably a 5 weeks old or more, such as C57BL/6, BALB/c or DBA/2, is used; $1 \times 10^5$ to $1 \times 10^8$ live cells are mixed with IFA, to give a mixture; and thereafter the above mouse is immunized with the resulting mixture. The antiserum used in the present invention shows high antibody titers against the cell membrane components and intracellular molecules of fungal cells. In contrast, the anti-*Candida* antisera generally used are not derived from mammals having infection resistance, and possess high antibody titers against the surface cell wall components, for instance, mannan and mannoprotein, which are different from the antiserum in the present invention.

The *Candida albicans* cells usable in the present invention are not particularly limited, and they include, for instance, *Candida albicans* TIMM 1768 strain and *Candida albicans* ATCC 10231 strain.

In the present specification, the phrase "recognized by antiserum" means binding to an antibody component contained in the antiserum, and the antigen can be detected and/or quantified by immunological procedures used for determining this binding, such as immunoblotting, ELISA, and immunoprecipitation. The binding of an antigen with an antibody is usually carried out at 4° C. to room temperature in an appropriate solution or gel, or on an antigen-immobilized plate.

These antigenic proteins are useful in mammals as antigens for vaccines for inducing resistance immunity to infection caused by *Candida*, represented by *Candida albicans*, and other fungal infections, and as antigens for diagnosing the presence or absence of infection and progression status thereof. In addition, the antigenic proteins are also useful as antigens in the method of prophylaxis, treatment and diagnosis of allergoses caused by fungi, represented by *Candida albicans*. In addition, because *Candida albicans* is a normally colonizing fungus in human bodies, most human immune cells (lymphocytes, macrophages, and the like) cause immune reactions, such as release of various cytokines and activation of immune cells in response to the antigenic proteins derived from *Candida albicans*.

Concretely, the antigenic protein of the present invention is useful as an antigen for releasing or activating effective immunoregulators, such as interferon Y and interleukin 4. Also, the antigenic protein of the present invention can be used as an antigenic component administered to individuals in, for example, provocation test, skin test, and nasal or eye mucosa test, for the purpose of in vivo diagnosis. Furthermore, the antigenic protein of the present invention can also be used as an antigenic component in laboratory diagnoses, including, for example, diagnostic methods based on agglutination reactions, precipitation reactions, neutralization reactions and labeled antibody techniques, which are antigen-antibody reactions; histamine release test; lymphocyte blast formation test; and leukocyte migration inhibition test.

The antigenic protein of the present invention is not particularly limited, as long as it is a protein or polypeptide, which are recognized by antiserum derived from a mammal having *Candida albicans*-infection resistance. The above protein or polypeptide can be obtained by immunoscreening for, for instance, an expression product of cDNA library from *Candida albicans* using antiserum derived from a mammal having *Candida albicans*-infection resistance.

Incidentally, the term "protein" in the present specification means a major component of living organisms, and refers to those comprising a polypeptide chain. In addition, the polypeptide in the present specification means those resulting from binding of a plurality of amino acids via peptide bonding, and the number of constituting amino acids is not particularly limited. In addition, the polypeptide in the present specification may be either a simple peptide comprising only amino acids, or a polypeptide complex comprising components other than the amino acids. Further, the term "fusion protein" is used in the present specification, which means a protein or polypeptide resulting from binding a partial or entire portion each of two or more proteins.

Concrete examples of the antigenic proteins include, for instance, the following polypeptides.

(A-1) a polypeptide having any one of amino acid sequences as shown in SEQ ID NOs: 1 to 9;

(A-2) a polypeptide having an amino acid sequence resulting from deletion, substitution, insertion or addition of one or more amino acids, for instance, one or several amino acids, in any one of the amino acid sequences as shown in SEQ ID NOs: 1 to 9;

(A-3) a polypeptide encoded by a nucleic acid having any one of the nucleotide sequences as shown in SEQ ID NOs: 10 to 18; and (A-4) a polypeptide encoded by a nucleic acid having a nucleotide sequence resulting from deletion, substitution, insertion or addition of one or more bases, for instance, one or several bases, in any one of the nucleotide sequences as shown in SEQ ID NOs: 10 to 18.

In addition, a protein immunologically equivalent to the antigenic protein mentioned above is encompassed in the present invention.

Here, the polypeptides each having the amino acid sequences as shown in SEQ ID NOs: 1 to 9 are each derived from a cDNA library of *Candida albicans* TIMM 1768 strain, obtained by immunoscreening each polypeptide using antiserum derived from a mammal having *Candida albicans*-infection resistance. In addition, in the immunoscreening, when an expression library of which host is *Escherichia coli* is used, the polypeptide is expressed as a simple peptide. Therefore, an antigenic protein is screened with an antibody against a polypeptide moiety by removing the influence of an antibody against sugar chains contained at a high level in anti-*Candida* serum.

The polypeptide having the amino acid sequence as shown in SEQ ID NO: 1 of Sequence Listing consists of 248 amino acids, and has homology to triosephosphate isomerase from *Saccharomyces cerevisiae* [T. Alber and G. Kawasaki, *Journal of Molecular and Applied Genetics*, 1, 419–434 (1982)]. Since N-terminus methionine is detached according to the results of N-terminus amino acid analysis of a protein isolated from *Candida albicans* cultured cells, it is considered that a part easily utilizable as an antigenic protein at least exists in a region from 2nd to 248th amino acids in SEQ ID NO: 1 of Sequence Listing. Further, when considered together with the results of homology analysis, the polypeptide as shown in SEQ ID NO: 1 of Sequence Listing is determined to be a full length structure of the triosephosphate isomerase of *Candida albicans*.

The polypeptide having the amino acid sequence as shown in SEQ ID NO: 2 of Sequence Listing consists of 132 amino acids, and has homology to a region (amino acid NOs: 10 to 137 amino acids) near the N-terminus of lysyl tRNA synthase from *Saccharomyces cerevisiae* [consisting of 590 amino acids, M. Mirande and J. P. Walker, *Journal of Biological Chemistry*, 263, 18443–18451 (1988)].

The polypeptide having the amino acid sequence as shown in SEQ ID NO: 3 of Sequence Listing consists of 548 amino acids, and a part of a region from 260th to 546th amino acids in the polypeptide has homology to a region of 523rd to 868th amino acids in SEQ ID NO: 3 of YCR030C on chromosome 3 from *Saccharomyces cerevisiae* [encoding a protein consisting of 870 amino acids; M. R. Red et al., *Yeast*, 7, 533–538 (1991)].

The polypeptide having the amino acid sequence as shown in SEQ ID NO: 4 of Sequence Listing consists of 175 amino acids, and has homology to EGD2 from *Saccharomyces cerevisiae* [consisting of 174 amino acids; M. Johnston et al., *Science*, 265, 2077–2082 (1994)].

The polypeptide having the amino acid sequence as shown in SEQ ID NO: 5 of Sequence Listing consists of 88 amino acids, and has homology to a region (amino acid NOs: 158 to 242) near the C-terminus of ATP synthase delta strand from *Saccharomyces cerevisiae* [consisting of 244 amino acids; J. Velours et al., *European Journal of Biochemistry*, 170, 637–642 (1988)].

The polypeptide having the amino acid sequence as shown in SEQ ID NO: 6 of Sequence Listing consists of 264 amino acids, and has homology to BMH2 from *Saccharomyces cerevisiae* [consisting of 272 amino acids; G. P. H. von Heusden et al., *European Journal of Biochemistry*, 229, 45–53 (1995)].

The polypeptide having the amino acid sequence as shown in SEQ ID NO: 7 of Sequence Listing consists of 224 amino acids, and has homology to a ribosomal YL8 protein from *Saccharomyces cerevisiae* [consisting of 243 amino acids; K. Mizuta et al., *Nucleic Acids Res.*, 20, 1011–1016 (1992)].

The polypeptide having the amino acid sequence as shown in SEQ ID NO: 8 of Sequence Listing consists of 115 amino acids, and a part of from 46th amino acid to the C-terminus in SEQ ID NO: 8 has homology to a part of 284th to 353rd amino acids of YNL083w from *Saccharomyces cerevisiae* [consisting of 494 amino acids; A. Soler-Mira et al., *Yeast*, 12, 485–491 (1996)].

The polypeptide having the amino acid sequence as shown in SEQ ID NO: 9 of Sequence Listing is a known HSP70 SSB type polypeptide, which has been found as an antigenic protein recognized by rabbit anti-*Candida* serum.

Its full length consists of 613 amino acids, and the polypeptide consisting of 280th to the C-terminus (333 amino acids) of SEQ ID NO: 9 is obtained as an antigenic protein [V. Maneu et al., *Yeast,* 13, 677–681 (1997)].

On the other hand, in the present invention, in the cDNA relating to the amino acid sequence as shown in SEQ ID NO: 9 of Sequence Listing, there are obtained four kinds of cDNAs exhibiting positive results in immunoscreening of the expression products, wherein each of these encodes a region of 320th amino acid to the C-terminus (294 amino acids); a region of 452nd amino acid to the C-terminus (162 amino acids); a region of 496th amino acid to the C-terminus (118 amino acids); and a region of 513th amino acid to the C-terminus (101 amino acids) in the amino acid sequence as shown in SEQ ID NO: 9 of Sequence Listing. Therefore, it is thought that a polypeptide of a length of at least 100 amino acids at the C-terminus is important to show the antigenicity. From the above, polypeptides having about 100 to about 294 amino acids containing at least 100 amino acids at the C-terminus, including the above four kinds of proteins, are encompassed in the antigenic protein of the present invention. In other words, in the amino acid sequence as shown in SEQ ID NO: 9 of Sequence Listing of the present invention, a polypeptide resulting from elimination of amino acids having a length of 319 to 512 amino acids from the N-terminus are encompassed in the antigenic protein in the present invention.

In the present invention, polypeptides having an amino acid sequence resulting from deletion, substitution, insertion or addition of one or more amino acids, for instance, one or several amino acids, in each of the polypeptides having any one of amino acid sequences as shown in SEQ ID NOs: 1 to 9 are encompassed in the antigenic protein of the present invention, as long as they are recognized by antiserum derived from a mammal having *Candida albicans*-infection resistance. Here, the term "several" refers to a number of several or greater. For instance, the antigenic proteins as shown in SEQ ID NO: 1 and SEQ ID NO: 2 are obtained as a fusion protein resulting from addition of a peptide comprising T7 tag at the N-terminus, and the protein or polypeptide resulting from addition of a peptide unrelated in the antigenicity as described above is encompassed in the antigenic protein of the present invention, and a polypeptide resulting from deletion of the T7 tagged portion is encompassed in the antigenic protein of the present invention. In addition, there is cited a polypeptide resulting from deletion of about 319 to about 512 amino acids from the N-terminus in the amino acid sequence as shown in SEQ ID NO: 9 in Sequence Listing as an example of deletion, which is encompassed in the antigenic protein in the present invention.

In addition, in the present invention, a polypeptide having a part of the amino acid sequences as shown in SEQ ID NOs: 1 to 9 of Sequence Listing is encompassed in the antigenic protein of the present invention, as long as they are recognized by antiserum derived from a mammal having *Candida albicans*-infection resistance. Further, polypeptides having an amino acid sequence resulting from deletion, substitution, insertion or addition of one or more amino acids, for instance, one or several amino acids, in an amino acid sequence having a part of the amino acid sequences are also encompassed in the antigenic protein of the present invention, as long as they are recognized by antiserum derived from a mammal having *Candida albicans*-infection resistance. In addition, a protein or polypeptide resulting from addition of a peptide unrelated in the antigenicity to these antigenic proteins of the present invention is encompassed in the antigenic protein of the present invention.

The polypeptide having a part of the amino acid sequences shown in SEQ ID NOs: 1 to 9 of Sequence Listing can be obtained, for instance, by using an antigenic protein having the amino acid sequences as shown in SEQ ID NOs: 1 to 9 of Sequence Listing as a raw material, cleaving the raw material by enzymatic digestion using a protease such as lysyl endopeptidase or trypsin, or cleaving by chemical treatment with cyanogen bromide or the like, and thereafter isolating and purifying a desired peptide fragment having the antigenicity by a known method in the purification of a protein. Further, the polypeptide can be also produced by chemical synthesis utilizing the peptide synthesis technique on the basis of the information on the chemical structure of the polypeptide obtained by the above method, or the like. In addition, the polypeptide can be produced by genetic engineering manipulations by using a nucleic acid encoding an amino acid sequence of the polypeptide.

As the means for carrying out deletion, substitution, insertion or addition of one or more, for instance, one or several amino acids, in an amino acid sequence, it would not be difficult to carry out such means by the use of various genetic engineering means described in *Molecular Cloning: A Laboratory Manual,* 2nd Ed. (published by Cold Spring Harbor Laboratory in 1989, edited by T. Maniatis et al.), or the like.

Each of the nucleotide sequences as shown in SEQ ID NOs: 10 to 18 of Sequence Listing is an example of a sequence for a nucleic acid encoding a polypeptide consisting of each of the amino acid sequences as shown in SEQ ID NOs: 1 to 9. Therefore, in the present invention, a protein or polypeptide recognized by antiserum derived from a mammal having *Candida albicans*-infection resistance, the polypeptide encoding a nucleic acid consisting of each of the nucleotide sequences as shown in SEQ ID NOs: 10 to 18 of Sequence Listing is encompassed in the antigenic protein of the present invention.

The nucleic acid is cDNA capable of expressing an antigenic protein obtained by immunoscreening of the expression library, wherein the cDNA is a full length of the gene, or has a partial nucleotide sequence. For instance, the nucleotide sequences as shown in SEQ ID NO: 10 and SEQ ID NO: 15 of Sequence Listing are full lengths of the antigenic protein genes, and the nucleotide sequences as shown in SEQ ID NO: 11, SEQ ID NO: 12, SEQ ID NO: 13, SEQ ID NO: 14, SEQ ID NO: 16, SEQ ID NO: 17, and SEQ ID NO: 18 of sequence Listing are partial sequences of the antigenic protein genes. For instance, when an antigenic protein derived from HSP70 SSB-type is the smallest antigenic protein of above, for instance, a polypeptide consisting of 101 amino acids from 513th to the C-terminus of the amino acid sequence as shown in SEQ ID NO: 9 of Sequence Listing, the antigenic protein encoded by the nucleic acid as shown in SEQ ID NO: 18 is encoded by the nucleotide sequence of 580th to 882nd bases of the nucleotide sequence of SEQ ID NO: 10. Therefore, it is preferable that a recombinant DNA encoding a portion having high antigenicity is designed to include 580th to 882nd bases of SEQ ID NO: 10 of the nucleotide sequence of Sequence Listing.

In addition, in the present invention, a polypeptide encoded by a nucleic acid having a nucleotide sequence resulting from deletion, substitution, insertion or addition of one or more bases, for instance, one or several bases, in each of the nucleotide sequences as shown in SEQ ID NOs: 10 to 18 of Sequence Listing is encompassed in the antigenic protein of the present invention, as long as the polypeptide is recognized by antiserum derived from a mammal having

*Candida albicans*-infection resistance. Here, the term "several" refers to a number of several or greater.

In order to carry out deletion, substitution, insertion or addition of one or more bases, for instance, one or several bases, in each of the nucleotide sequences as described above, there may be utilized various known genetic engineering manipulations, including, for instance, gapped duplex method [Wilfried, K. et al., *Nucleic Acids Research*, 12, 9441–9456 (1984)], deletion method [Celeste, Y. P. et al., *Methods in Enzymology*, 154, 367–382 (1987)], uracil DNA method [Thomas, A. K. et al., *Gene*, 34, 315–323 (1987)], cassette mutation method [James, A. W. et al., *Gene*, 34, 315–323 (1985)], and the like.

In addition, a protein derived from *Candida albicans* mutant, a closely related species (for instance, fungi belonging to the genus *Candida*), and fungi other than *Saccharomyces cerevisiae*, protein or polypeptide having characteristics which are immunologically equivalent to the antigenic protein of the present invention is encompassed in the antigenic protein of the present invention. The term "protein having characteristics which are immunologically equivalent" in the present specification means a protein or polypeptide which is recognized by an antibody contained in antiserum derived from a mammal immunized by the antigenic protein of the present invention having any one of the amino acid sequences as shown in SEQ ID NOs: 1 to 9 and has different modification in the amino acid sequence or sugar chain.

Incidentally, the antigenic protein of the present invention may be modified to give a derivative, for the purpose of enhancement of induction of individual prophylactic immunocompetent, the decrement of allergic reaction or disappearance of enzyme activity, when used in enhancement of stability and/or enhancement of a desired reactivity as an antigen, namely when used in treatment; or for the purpose of enhancement of specific binding of an antigen with an antibody, when used for diagnosis. The modification method includes, for instance, pyridylethylation, reduction, alkylation, acylation, chemical coupling to an appropriate material, mild formalin treatment or guanidine hydrochloride treatment. As the method for preparing the derivative, for instance, by using polyethylene glycol (PEG) method [Wie et al., *Int. Arch. Allergy Appl. Immunol.*, 64, 84–99 (1981)], the antigenic protein may be allowed to bind with PEG.

2. Nucleic Acid of Present Invention

The nucleic acid of the present invention is a nucleic acid encoding an antigenic protein which is recognized by antiserum derived from a mammal having *Candida albicans*-infection resistance.

The above nucleic acid can be obtained, for instance, in the same manner as the antigenic protein of the present invention, by preparing cDNA expression library from *Candida albicans*, and immunoscreening the expression library by using antiserum derived from a mammal having *Candida albicans*-infection resistance. In addition, the nucleic acid can be also obtained by preparing a genomic library or cDNA library of *Candida albicans*, and screening of the library by using an oligonucleotide as a probe, the oligonucleotide being deduced to encode a part of the amino acid sequence of the antigenic protein of the present invention.

The nucleic acid of the present invention is useful as an antigen gene for vaccines for inducing resistance immunity against infections caused by *Candida*, represented by *Candida albicans*, and other fungal infections; and as an antigen gene for prophylaxis, treatment and diagnosis of allergoses caused by fungi, represented by *Candida albicans*.

Concrete examples of the nucleic acid of the present invention, for instance, include the following nucleic acids:

(B-1) a nucleic acid encoding a polypeptide having any one of amino acid sequences as shown in SEQ ID NOs: 1 to 9;

(B-2) a nucleic acid encoding a polypeptide having an amino acid sequence resulting from deletion, substitution, insertion or addition of one or more amino acids, for instance, one or several amino acids, in any one of the amino acid sequences as shown in SEQ ID NOs: 1 to 9;

(B-3) a nucleic acid having any one of nucleotide sequences as shown in SEQ ID NOs: 10 to 18;

(B-4) a nucleic acid having an nucleotide sequence resulting from deletion, substitution, insertion or addition of one or more bases, for instance, one or several bases, in any one of nucleotide sequences as shown in SEQ ID NOs: 10 to 18; and (B-5) a nucleic acid capable of hybridizing with a nucleic acid according to any one of (B-1) to (B-4), or a nucleic acid complementary thereto, under stringent conditions.

Here, the nucleic acid may be either DNA or RNA.

Each of the nucleotide sequences shown in SEQ ID NOs: 10 to 18 of Sequence Listing is an example of a sequence of a nucleic acid encoding a polypeptide having the amino acid sequences as shown in SEQ ID NOs: 1 to 9.

Incidentally, there has been known that 1 to 6 codons (triplet base combination) designating a particular amino acid on a gene exist for every amino acid. Therefore, there can be a large number of kinds of nucleic acids each encoding an amino acid sequence, depending on its amino acid sequence. In nature, the nucleic acid does not exist in a stable form, and it is not rare that a mutation of its nucleotide sequence takes place. The mutation on the nucleic acid may not affect the amino acid sequence encoded thereby (so-called "silent mutation"), in which case the nucleic acid having the above mutation can be said as different nucleic acids encoding the same amino acid sequence. There cannot, therefore, be denied the possibility that even when the nucleic acid encoding a particular amino acid sequence is isolated, a variety of nucleic acids encoding the same amino acid sequence are produced with generation passage of the organism containing them. Moreover, it is not difficult to artificially produce a variety of the nucleic acids encoding the same amino acid sequence by means of various genetic engineering manipulations.

For example, when a codon used on a natural DNA encoding the desired protein is low in usage in the host in the production of a protein by genetic engineering, the expression level of the protein is sometimes low. In such a case, high expression of the desired protein is achieved by artificially converting the codon into another one of commonly used in the host without changing the amino acid sequence encoded (for example, Japanese Examined Patent Publication No. Hei 7-102146). It is of course possible to artificially produce a variety of nucleic acids encoding a particular amino acid sequence, and the nucleic acids can be also produced in nature.

From the above, the nucleic acid encoding a polypeptide having each of the amino acid sequences as shown in SEQ ID NOs: 1 to 9, which are given in (B-1) in the present specification is not limited to the nucleic acid having each of the nucleotide sequences as shown in SEQ ID NOs: 10 to 18, which are given in (B-3).

Therefore, in the present invention, a nucleic acid having a nucleotide sequence resulting from deletion, substitution, insertion or addition of one or more bases, for instance, one or several bases in each of the nucleotide sequences as shown in SEQ ID NOs: 10 to 18 of Sequence Listing is also encompassed in the nucleic acid of the present invention, as long as its expression product is recognized by antiserum derived from a mammal having *Candida albicans*-infection resistance. Here, the term "several" refers to a number of several or greater.

For instance, there are also encompassed in the nucleic acid of the present invention a nucleic acid, which is a derivative of a nucleic acid as shown in SEQ ID NOs: 10 to 18 of Sequence Listing, the nucleic acid encoding a protein resulting from appropriate detachment of a part of the protein with retaining the antigenicity of each of the antigenic protein having the amino acid sequences as shown in SEQ ID NOs: 1 to 9 of Sequence Listing, or a nucleic acid encoding a fusion protein of the antigenic protein in which another polypeptide, for instance, a protein derived from T7 phage, histidine tag, maltose binding protein, glutathione-S-transferase, β-galactosidase, or the like is added.

Further, a nucleic acid capable of hybridizing with a nucleic acid as shown in any one of (B-1) to (B-4), or with a nucleic acid complementary thereto, under stringent conditions, the nucleic acid encoding an antigenic protein which is recognized by antiserum derived from a mammal having *Candida albicans*-infection resistance [i.e. the nucleic acid of (B-5)] is also encompassed in the nucleic acid of the present invention. The above nucleic acid can be detected as follows.

In other words, a membrane immobilized with the nucleic acid to be detected is incubated at 50° C. for 12 to 20 hours together with a probe in 6×SSC (wherein 1×SSC has 0.15 M NaCl, 0.015 M sodium citrate, pH 7.0) containing 0.5% by weight SDS, 0.1% by weight bovine serum albumin (BSA), 0.1% by weight polyvinyl pyrrolidone, 0.1% by weight of a synthetic, water soluble, nonionic copolymer of sucrose and epichlorhydrin having a molecular weight of about 400,000 (FICOLL® 400), and 0.01% by weight-denatured salmon sperm DNA. After termination of the incubation, the membrane is washed, initiating under the conditions of 37° C. in 2×SSC containing 0.5% by weight SDS, the SSC concentration being made variable up to a range of 0.1×SDS, and the temperature being variable up to a range of 50° C., until a signal ascribed to an immobilized nucleic acid can be distinguished from the background, and thereafter the probe is detected. When the nucleic acid is detected under the conditions described above, the nucleic acid is referred to "a nucleic acid capable of hybridizing under stringent conditions." The probe used herein is a part of a nucleic acid as shown in any one of (B-1) to (B-4), or a part of a nucleic acid complementary thereto.

The nucleic acid described above includes, for instance, a nucleic acid capable of hybridizing with a nucleic acid as shown in any one of (B-1) to (B-4), or a nucleic acid complementary thereto, under stringent conditions, possessed by mutants and closely related fungi of *Candida albicans* (for instance, the fungi of the genus *Candida* such as *Candida tropicalis*), the nucleic acid encoding a protein having immunologically equivalent antigenicity.

In addition, in the nucleic acid of the present invention, a nucleic acid accompanied by its mutant form, allele, homologue gene, degeneracy of codon in a nucleic acid encoding a polypeptide having any one of the amino acid sequences as shown in SEQ ID NOs: 1 to 9, or a nucleic acid encoding a polypeptide having an amino acid sequence resulting form deletion, substitution, insertion or addition of one or more amino acids, for instance, one or several amino acids, in any one of the amino acid sequence as shown in SEQ ID NOs: 1 to 9 is encompassed in the nucleic acid of the present invention, as long as its expression product is recognized by antiserum derived from a mammal having *Candida albicans*-infection resistance.

Further, the nucleic acid of the present invention includes a nucleic acid encoding an antigenic protein recognized by antiserum derived from a mammal having *Candida albicans*-infection resistance, for instance, a nucleic acid specifically binding to the nucleic acids shown in (B-1) to (B-5). Here, the nucleic acid of the present invention may be labeled with a known fluorescent substance or radioactive substance. The nucleic acid can be utilized for a probe used for detection of an antigenic protein gene of *Candida albicans* by hybridization, or for a primer in a method for amplifying DNA using the DNA polymerase.

3. Vector and Transformant of Present Invention

The vector of the present invention is a vector comprising the nucleic acid of the present invention. Such a vector enables a host such as *Escherichia coli* to stably harbor the nucleic acid of the present invention. The vector usable for construction of the above vector includes, for instance, pUC118, pWH5, pTV118, PSCREEN-1B, and the like, and the vector is not particularly limited as long as it is a vector in which the nucleic acid of the present invention can be inserted and expressed. In addition, the DNA of the present invention can be used by ligating to an appropriate expression vector, to give recombinant DNA for expression. In the present invention, each of the nucleic acids having the nucleotide sequences as shown in SEQ ID NOs: 10 to 18 is used by ligating to PSCREEN-1B, and thereafter introducing the resulting product as recombinant DNA for expression into *Escherichia coli*. The method for inserting a nucleic acid into a vector is not particularly limited, and there can be employed a known method, such as a method using T4 DNA ligase.

The transformant of the present invention is those resulting from transformation with the vector of the present invention. The transformant described above is obtained by introducing the vector of the present invention into a host. As the host, there can be used insect cells and animal cells such as COS-7 and Vero cells, in addition to bacteria such as *Escherichia coli,* the genus *Bacillus* and the like, yeasts such as *Saccharomyces cerevisiae,* fungi such as the genus *Aspergillus, Pichia pastoris.* The method for introducing a vector into a host include known methods, for instance, calcium phosphate method, $CaCl_2$ method, DEAE dextran method, electroporation method, and the like. The above transformant can be selected by, for instance, using as an index a selection marker in the used vector. In addition, there can be confirmed that a desired nucleic acid is introduced by, for instance, hybridization using a nucleic acid extracted from the transformant and a probe capable of specifically detecting the nucleic acid of the present invention.

The transformant described above can be utilized when the nucleic acid of the present invention is prepared and when the antigenic protein of the present invention is prepared.

4. Method for Producing Antigenic Protein of Present Invention

The method for producing an antigenic protein which is recognized by antiserum derived from a mammal having *Candida albicans*-infection resistance of the present invention is characterized in that the method comprises culturing the transformant of the present invention under conditions capable of expressing an antigenic protein encoded by the nucleic acid of the present invention.

The culture conditions are not particularly limited. For instance, in a case of a transformant obtained by using lambda phage vector λSCREEN™-1 and Phage Maker™ System Phage Pack Extract [both manufactured by Novagen], the transformant may be cultured in LB medium containing ampicillin utilized as a selective pressure, and induced-expression by IPTG (isopropyl-thio-β-D-galactoside) in an appropriate timing. In a transformant obtained by using other vectors and hosts, the transformant may be also cultured under appropriate conditions capable of expressing proteins in the medium to which an appropriate selective pressure is applied. The desired protein is expressed by culturing in the manner described above.

The expressed protein or polypeptide can be collected and purified by a known protein purification method in the field of art. In addition, the presence or absence of the antigenicity of the resulting protein or polypeptide can be confirmed by immunological techniques, for instance, immunoblotting method, ELISA, immunoprecipitation method, and the like.

In addition, the antigenic protein of the present invention may be produced from the transformant of the present invention obtained by genetic engineering manipulations, or the antigenic protein may be obtained from *Candida albicans* culture by a known protein purification method.

5. Pharmaceutical Composition and Diagnostic Composition of Present Invention

The pharmaceutical composition and diagnostic composition of the present invention are 1) those comprising the antigenic protein of the present invention, or an antigenic protein obtained by the method of the present invention, and 2) those comprising the nucleic acid of the present invention.

1) Pharmaceutical Composition and Diagnostic Composition Each Comprising Antigenic Protein of Present Invention, or Antigenic Protein Obtained by Method of Present Invention.

In the pharmaceutical composition and diagnostic composition of the present invention, there are encompassed a vaccine for inducing in mammals resistance immunity to infection caused by *Candida*, represented by *Candida albicans*, and other fungal infection, and a diagnostic composition for diagnosing the presence or absence of infection and progression status thereof. Further, compositions used for prophylaxis, treatment and diagnosis of allergoses caused by fungi, represented by *Candida albicans* are also encompassed. In addition, because *Candida albicans* are normally colonized in human bodies, most human immune cells (lymphocytes, macrophages, and the like) cause immune reactions, such as release of various cytokines and activation of immune cells, to the antigenic proteins derived from *Candida albicans*. In other words, in the pharmaceutical composition and diagnostic composition of the present invention, there are also encompassed compositions for releasing or activating effective immunoregulators, such as interferon Y and interleukin 4.

The composition for inducing the resistance immunity to infection is generally employed as a preparation in the form of a suspension or solution of the antigenic protein of the present invention containing the following adjuvant, in order to acquire further enhanced humoral immunity and/or cellular immunity. The adjuvant is usually administered together with the antigenic ingredients, and the adjuvant may be administered before or after administration of the antigenic ingredients.

The adjuvant appropriate for vaccination to mammals includes complete or incomplete Freund's adjuvant; inorganic gels made of aluminum hydroxide, alum and the like; detergents such as lysolecithin and dimethyloctadecylammonium bromide; polyanions such as dextran sulfate and poly-IC; peptides such as muramyl peptide and tuftsin; monophosphoryl lipid A (MPL) manufactured by Ribi; and B subunit of cholera toxin, without being limited thereto. The antigen can be administered by incorporating it in liposome or other microcarriers. There can be of course used a mixture of several different antigenic proteins.

The composition for prophylaxis, treatment and diagnosis of allergoses may be used in a form of an appropriate salt solution or suspension of the antigenic protein of the present invention. In some cases, polyethylene glycol and phenol may be added thereto. Further, the composition may be a suspension or solution containing the adjuvant described above. The adjuvant is usually administered together with the antigen, and the adjuvant may be administered before or after administration of the antigen. The antigen can be administered by incorporating it in liposome or other microcarriers.

The pharmaceutical composition of the present invention may be formulated with various additives as occasion demands, and its form can have various preparation forms. The above additives include additives for preparation for the purpose of forming a desired preparation form. Examples of these additives include, for instance, nutrients such as ascorbic acid, biotin, calcium pantothenate and niacin; covering agents such as sodium metaphosphate, sodium phosphates (primary, secondary, tertiary salts) and sodium pyrophosphate; preservatives such as calcium sorbate and benzoic acid; other additives and diluents such as Arabic rubber, traganth, sodium alginate, mannitol, sorbitol, lactose, fructose, soluble starches, amino acids, glucose, sucrose, honey, and fatty acid esters.

The pharmaceutical composition of the present invention can be administered orally or non-orally. For instance, the pharmaceutical composition may be made into a preparation form suitable for oral administrations such as powder, granule, pellet, tablets, coating agents, capsules, solutions and syrup; and preparation forms suitable for non-oral administrations such as injection, drops, suppository, ophthalmic solutions, collunarium and spray.

When the pharmaceutical composition of the present invention is particularly used as vaccines, there may be added as occasion demands a stabilizer such as human serum albumin, gelatin and amino acids in an appropriate concentration, and a preservative such as phenol and thimerosal in an appropriate concentration. In addition, the pharmaceutical composition may be used as a solution preparation, or a dry preparation by lyophilizing the composition. The dry preparation may be suspended with an appropriate solvent upon use such as distilled water for injection.

As a method for administering the pharmaceutical composition, the pharmaceutical composition may be administered orally, transmucosally (nasally, intravaginally or the like), percutaneously (subcutaneously or intracutageneously), or intravenously. Representative dosage is preferably in a range of 0.01 to 5.0 mg/kg body weight as an amount of protein, and more preferably in a range of 1 µg to 100 µg/kg body weight. As occasion demands, the dosage may be increased, or the number of dosage may be increased.

The diagnostic composition used against individuals for the purpose of in vivo diagnosis in, for instance, provocation test, skin test, or nasal or eye mucosa test includes those in which the antigenic protein of the present invention is made into a form of lyophilized powder or in a form of an appropriate salt solution or suspension, and polyethylene glycol or phenol may be added to such compositions. For patch tests, the antigenic protein of the present invention may be mixed with white petrolatum as a base material supplemented with a detergent such as sodium lauryl sulfate. In addition, in a case of using as an antigen for assaying IgE titer, the above antigenic protein can be used by immobilizing the antigenic protein on a solid material such as a paper disc, a cellulose sponge, or a microplate.

2) Pharmaceutical Composition and Diagnostic Composition Comprising Nucleic Acid of Present Invention The pharmaceutical composition and diagnostic composition of the present invention can be used in mammals as vaccines for inducing resistance immunity to infection caused by *Candida*, represented by *Candida albicans*, and other fungal infection, and can be used for prophylaxis, treatment and diagnosis of allergoses caused by fungi, represented by *Candida albicans*. When the composition is used for the protection to infection and the treatment of allergoses, a plasmid carrying the nucleic acid of the present invention at downstream of an appropriate promoter may be directly used, or may be prepared in the form of an appropriate salt solution or suspension after its incorporation into retrovirus or adenovirus, such that the nucleic acid of the present invention is capable of expressing in mammalian cells. In addition, the nucleic acid of the present invention may be incorporated in the liposome or other microcarriers, or it may be mixed with an appropriate polycationic lipid.

As the above nucleic acid, there may be employed those including chemical modifications which allow to enhance the migration ability into the cells or the stability within the cells. The chemical modifications include, for instance, derivatives derived from phosphorothioate, phosphorodithioate, alkyl phospho triesters, alkyl phosphonates, alkyl phosphamidates and the like.

As a method for administering the pharmaceutical composition, the pharmaceutical composition may be administered intramuscularly, subcutaneously, intravenously, orally, intrarectally, percutaneously, nasally, hypoglosally, intraperitoneally, or the like. Representative dosage is preferably in a range of 0.01 μg to 10 mg/kg body weight as an amount of the nucleic acid, and more preferably in a range of 1 μg to 5 mg/kg body weight. As occasion demands, the dosage may be increased, or the number of dosage may be increased.

6. Antibody or Antibody Fragment of Present Invention

The antibody of the present invention is an antibody capable of specifically binding to the antigenic protein of the present invention. Here, as the antibody, an antibody fragment is also encompassed, as long as the antibody fragment is capable of specifically binding to the antigenic protein of the present invention.

The antibody of the present invention can be obtained by a conventional method, and it may be either a polyclonal antibody or monoclonal antibody. In addition, in the present invention, the antibody may be a single-chain antibody capable of specifically binding to the antigenic protein of the present invention. The antibody or the antibody fragment can be utilized for detection of fungi of the infectious diseases of *Candida albicans* or closely related fungi, or it can be utilized for identification of allergens in allergoses caused by *Candida albicans* or closely related fungi.

When the antibody or antibody fragment of the present invention is used for detection of fungi of infectious diseases, identification of allergens in allergoses, and the like, the nucleic acid may be labeled with a known fluorescent substance or radioactive substance.

In addition, the antibody can be used for purification of the antigenic protein of the present invention. In this case, for instance, the antigenic protein of the present invention can be more easily purified by immobilizing the antibody or antibody fragment of the present invention to a carrier or the like.

7. Nucleic Acid Capable of Specifically Binding to Nucleic Acid Encoding Antigenic Protein of Present Invention The nucleic acid capable of specifically binding to a nucleic acid encoding the antigenic protein of the present invention can be utilized for a probe used in detection of a nucleic acid encoding the antigenic protein of the present invention by hybridization, or it can be utilized for a primer used for detection by a method for amplifying DNA using the DNA polymerase. The nucleic acid capable of specifically binding to a nucleic acid encoding the antigenic protein of the present invention includes those binding to sense side or antisense side of the nucleic acid encoding the antigenic protein. The nucleic acid may be labeled with a known fluorescent substance or radioactive substance.

EXAMPLES

The present invention is hereinafter described in more concretely by means of the following examples, without intending to limit the present invention to these examples.

Example 1

Induction of Infection Resistance and Involvement of CD4-Positive T-Cells in Infection Resistance 1) Induction of Infection Resistance

*Candida albicans* (*C. albicans*) TIMM 1768 was cultured overnight with shaking in Sabouraud dextrose medium. Thereafter, cultured cells were harvested by centrifugation and washed with physiological saline. The obtained cells were suspended in physiological saline so as to have concentrations of $1 \times 10^6$, $1 \times 10^7$, and $1 \times 10^8$ cells/ml. An equal volume of IFA (incomplete Freund's adjuvant) was added to each suspension and mixed. This mixture was subcutaneously administered to C57BL/6 mice at 0.1 ml per animal, thereby immunizing the mice with live *Candida* cells. After 1 week, the mice were further immunized by subcutaneously administering the same number of live *Candida* cells prepared in the same manner as above. Therefore, each mouse was twice immunized with $5 \times 10^4$, $5 \times 10^5$, or $5 \times 10^6$ live *Candida* cells. As a control, a mixture of physiological saline and an equal volume of IFA, the physiological saline being used in place of a suspension of live *Candida* cells, was twice administered subcutaneously at an interval of 1 week.

One week after the second immunization, all immunized mice and control mice were infected by intravenous administration of $2.5 \times 10^5$ *C. albicans* TIMM 1768 cells obtained by culturing in Sabouraud-dextrose medium. After infection, the mice were observed for life or death for 30 days. The results are shown in Table 1.

TABLE 1

| Administration | Dosage at One Time | Mean Survival Days ± SD | Number of Live Mice after 30 days/ Number of Mice Used |
|---|---|---|---|
| Physiological Saline | — | 4.0 ± 1.4 | 0/5 |
| Live Cells | $5 \times 10^4$ | 16.8 ± 6.3 | 0/5 |
|  | $5 \times 10^5$ | 19.6 ± 9.0 | 0/5 |
|  | $5 \times 10^6$ | >20.8 ± 10.1 | 2/5 |

Table 1 shows that all control mice (non-immunized mice) died within 10 days at the dose levels mentioned above, whereas the immunized mice acquired obvious resistance to infection.

2) Acquisition of Infection Resistance by CD4-Positive T Cells

An anti-CD4 antibody (prepared from ATCC TIB207) or anti-CD8 antibody (prepared from ATCC TIB105) was intraperitoneally administered to BALB/c mice that had been twice immunized by $5 \times 10^6$ live Candida albicans cells at an interval of 1 week in the same manner as in item 1) above, at 0.3 mg per animal 3 times in total at 23, 26, and 29 days after the final immunization. At 29 days after final immunization, $1 \times 10^5$ C. albicans TIMM 0136 cells obtained by culturing in Sabouraud-dextrose medium were intravenously administered. As a control, non-immunized mice, and mice immunized without administering any antibody, were prepared, and these mice also were intravenously administered with $1 \times 10^5$ C. albicans TIMM 0136 cells in the same manner as above, respectively. At 7 days after administration, the number of live C. albicans cells in the kidney was determined.

The anti-CD4 antibody and anti-CDB antibody were purified by a conventional method from ascitic fluid in which hybridomas were proliferated by injecting hybridomas intraperitoneally to scid mice. In addition, by using a flow cytometer (manufactured by Ortho Diagnostic), it was confirmed that the obtained antibody could eliminate respective cells.

As a result, it is concluded that the decrease of the Candida cell number in the kidney is significantly inhibited by the administration of the anti-CD4 antibody, indicating that CD4-positive T-cells play an important role in the infection resistance.

Example 2

Collection of Serum from Mammal Having Infection Resistance, Characteristics Thereof, and Preparation of Various Absorption Sera 1) Collection of Serum from Infection-Resistant Mammal Serum was collected from BALB/c mice that were immunized 3 times with $5 \times 10^6$ live C. albicans TIMM 1768 cells in a mixture with CFA (complete Freund's adjuvant) in the same manner as in item 2) of Example 1 by a conventional method at 7 days after final immunization. This resulting serum was used as an anti-Candida serum.

2) Characteristics of Serum from Infection-Resistant Mammal

The characteristics of the anti-Candida serum obtained in item 1) of Example 2 were studied.

First, as antigenic components, C. albicans cell wall fraction (CW), cytoplasm fraction (HSS), and cell membrane fraction (LSP) were prepared.

A loopful of C. albicans TIMM 1768 cells in Sabouraud agar slant culture was transferred to a test tube containing 5 ml of YPD medium (1% by weight yeast extract, 2% by weight polypeptone, 2% by weight glucose). After culturing with shaking at 30° C. for 24 hours, 50 µl of the resulting culture was inoculated to 500 ml of YPD medium contained in a 2-liter conical flask and cultured overnight with shaking at 35° C. A total of four such 2-liter conical flasks were used to culture.

Cells were harvested by centrifugation at $2,000 \times g$ for 10 minutes from about 2 liters of the culture obtained (about $7 \times 10^7$ cells/ml). The cells were washed twice with 500 ml of sterilized water, and then washed once with 500 ml of the SSB solution (50 mM phosphate buffer, pH 7.5, containing 0.8 M sorbitol). After the cells were suspended in about 500 ml of the SSB solution, 70 ml of SSB solution containing 100 mM EDTA, and 1 ml of 2-mercaptoethanol were added thereto, and then gently shaken. Subsequently, 70 ml of SSB solution containing 3.3 mg of ZYMOLYASE® 20T (manufactured by Seikagaku Corporation) per 1 ml was added to the resulting suspension, and then gently shaken at 35° C. for 1 hour. Further, 70 ml of SSB solution containing 12 mg of Trichoderma Lysing Enzyme (manufactured by Sigma) per 1 ml was added, and then gently shaken at 35° C. for 1 hour. The suspension obtained was centrifuged at $2,000 \times g$ for 10 minutes to harvest protoplast cells, while the supernatant was taken as the cell wall fraction (CW).

One-hundred and forty milliliters of sterile physiological saline was added to the protoplast cells obtained in the manner described above (the protoplast cells contained per 1 ml of this suspension being about $1 \times 10^9$ cells), and then stirred well. Thereafter, the mixture was allowed to stand on ice for 10 minutes. After confirming that the protoplast cells bursted, the mixture was centrifuged at $10,000 \times g$ for 30 minutes, and the precipitate obtained was taken as an insoluble fraction (referred to as LSP). The centrifugal supernatant was further centrifuged at $100,000 \times g$ for 60 minutes, and the supernatant obtained was taken as the soluble fraction (referred to as HSS). After suspending the LSP in 140 ml of physiological saline, the resulting suspension was subjected to sonication treatment, and then sterilized by heat treatment in a boiling water bath for 5 minutes, to give an LSP antigen solution containing membrane proteins and the like. In addition, the CW was also subjected to sonication and heat treatments in the same manner as above, to give a CW antigen solution. As to the HSS, it was used without any treatment as an HSS antigen solution.

The protein concentrations of the LSP antigen solution, the HSS antigen solution, and the CW antigen solution obtained in the manner as described above were 2.3 mg/ml, 3.5 mg/ml, and 2.1 mg/ml, respectively (the amount of protein was quantified by using bicinchonic acid (BCA) reagent with BSA as a standard).

Each of the CW antigen solution, the LSP antigen solution, and the HSS antigen solution obtained as antigenic components was diluted with PBS so as to have a protein concentration of 10 µg/ml. Thereafter, 50 µl of each dilution was added to IMMUNO-MODULE (manufactured by Nunc), and each of the IMMUNO-MODULE was allowed to stand at 4° C. overnight to coat them with the respective antigens. The coated IMMUNO-MODULE was subjected to blocking treatment by using PBS solution containing 1% by weight bovine serum albumin. Next, 50 µl of a 60-fold diluted anti-Candida serum or control serum was added to each IMMUNO-MODULE. The mixture was incubated at 37° C. for 1 hour, and thereafter incubated with a peroxidase-labeled anti-mouse IgG antibody (2,000-fold diluted) at 37° C. for 1 hour. After incubation, the mixture was washed with PBS, and a substrate solution was then added thereto. After 15 minutes, the absorbance at 405 nm was determined. The higher the absorbance shows the larger the amount of antigen-recognizing antibody, i.e. the higher the antibody titer against the antigen. The results are shown in Table 2. The above control serum was prepared from serum derived from a mouse administered with a mixture of physiological saline and an equal volume of CFA, the physiological saline being used in place of live cells, in 3 times subcutaneously at intervals of 1 week.

TABLE 2

| Antigen Fraction | Absorbance | |
| --- | --- | --- |
| | Anti-*Candida* Serum | Control Serum |
| CW | 0.013 | 0.006 |
| LSP | 0.051 | 0.006 |
| HSS | 0.237 | 0.006 |

As is evident from Table 2, there was elucidated that the anti-*Candida* serum has the highest antibody titer against the HSS but possesses an antibody titer against the LSP as well. The antibody titer against the CW was low.

Example 3

Screening of *C. albicans* cDNA Expression Library for Antigenic Proteins

1) Preparation of *C. albicans* cDNA Expression Library

Total RNA was extracted and purified from cells to prepare a cDNA expression library for *C. albicans* TIMM 1768 strain. Specifically, the above strain was cultured at 35° C. in 200 ml of YPD medium, and thereafter the cells were harvested by centrifugation (2,000 rpm, 5 minutes) and washed once with distilled water. The cells were quickly frozen with liquid nitrogen, and the frozen cells were disrupted with a mortar into a powdery form. Total RNA was recovered and purified from this cell powder using an RNA extraction kit (manufactured by Pharmacia). poly(A)+ RNA was prepared using Oligotex™-dT30 <Super> (manufactured by Takara Shuzo Co., Ltd.) from this total RNA. cDNA was synthesized from 5 μg of the poly(A)+ RNA using cDNA synthesis kit (manufactured by Takara Shuzo Co., Ltd.). A cDNA library was constructed by ligating the synthesized cDNA to lambda phage vector λSCREEN™-1 (manufactured by Novagen), and thereafter carrying out in vitro packaging by using Phage Maker™ System PhagePack Extract (manufactured by Novagen).

2) Immunoscreening of Antigenic Proteins Recognized by the Anti-*Candida* Sera Resulting from Immunization with Live *C. albicans* Cells Phage clones expressing proteins reactive with the antisera resulting from immunization with live *C. albicans* cells were detected by immunoscreening. In the cDNA library prepared by phage vector λSCREEN™-1, the cDNA was expressed as a fusion protein with a peptide comprising the T7 tagged sequence etc., or a polypeptide initiating from the translation initiation codon in the cDNA.

Specifically, the cDNA library was inoculated to host *Escherichia coli* BL21(DE3)pLysE strain and mixed with top agarose (LB medium containing 0.7% by weight agarose). Thereafter, the mixture was overlayered on a plate of 2×YT (1.6% by weight Bacto-tripton, 1% by weight yeast extract, 0.5% by weight NaCl) and cultured at 37° C. for 6 hours, to form phage plaques. A nylon membrane (Hybond™-N, manufactured by Amersham) was superposed on the resulting plaque, and thereafter allowed to stand overnight at 4° C. and subsequently incubated at 37° C. for 4 hours. The membrane was removed from the plate, and then washed with PBST (composition: 100 mM NaCl, 10 mM phosphate buffer, pH 7.5, 0.1% Tween® 20) for 10 minutes, and thereafter blocked by immersing the membrane in an appropriate amount of Block Ace (manufactured by Dainippon Pharmaceutical). This membrane was allowed to stand at room temperature overnight, and thereafter incubated with the anti-*Candida* serum prepared in item 1) of Example 2 (500-fold dilution) at room temperature for 3 hours. After incubation, the membrane was washed, and thereafter incubated with a peroxidase-labeled anti-mouse IgG antibody (1,000-fold dilution) at room temperature for 1 hour. After incubation, the membrane was washed, and then allowed to generate luminescence by using SuperSignal® Substrate Western Blotting (manufactured by Pierce), thereby detecting phage plaques reactive to the anti-*Candida* serum.

As a result of a screening of $5 \times 10^4$ plaques, there were found 100 to 150 phage plaques reactive with the antiserum. Among them, plaques showing a particularly strong reaction were remarked and further cloned. Automatic subcloning took place in host *Escherichia coli* BM25.8 strain by inoculating the cloned phage to the strain, whereby a cDNA-containing region existing in the phage DNA was automatically subcloned into a plasmid DNA. The plasmid was purified from *Escherichia coli* harboring this plasmid, and the nucleotide sequence of the cDNA was determined. As a result of the nucleotide sequence analysis, it was found that two clones were novel genes having homologies to triosephosphate isomerase from *Saccharomyces cerevisiae* (*S. cerevisiae*), and had full-length cDNA. Also found were one clone each of novel genes having homology to lysyl-tRNA synthetase from *S. cerevisiae* and DNA 98 on chromosome 3 of *S. cerevisiae*. These cDNAs contained a part of the respective genes, and the presence of antigenic determinants reactive with the antiserum in these regions was clarified.

The nucleotide sequences of the above novel genes, i.e., the *S. cerevisiae* triosephosphate isomerase homologue gene, the *S. cerevisiae* lysyl-tRNA synthetase homologue gene, and the homologue gene to DNA 98 on chromosome 3 of *S. cerevisiae*, are respectively as shown in SEQ ID NO: 10, SEQ ID NO: 11, and SEQ ID NO: 12 in Sequence Listing. From the above nucleotide sequences, these nucleic acids encode the polypeptides comprising the amino acid sequences respectively as shown in SEQ ID NO: 1, SEQ ID NO: 2, and SEQ ID NO: 3 in Sequence Listing.

3) Screening for *C. albicans* Antigenic Proteins Using Absorption Anti-*Candida* Serum The cDNA library described in item 1) above was immunoscreened for *C. albicans* antigenic proteins using an absorption antiserum from the serum immunized with live *C. albicans* cells. Specifically, a solution in which the anti-*Candida* serum, the HSS, and the CW were mixed, in a 1:1:1 (v/v/v) ratio, was prepared and used as an absorption antiserum.

Antigenic molecules were screened in the same manner as in item 2) of Example 3 using this absorption antiserum. The antiserum used was a 500-fold dilution of the absorption antiserum. Phage plaques reactive with this antiserum were further cloned. As a result of the nucleotide sequence analysis of the cloned cDNA, it was clarified that one clone comprises a nearly full length of a novel gene having homology to the *S. cerevisiae* EGD2 gene, and the other clone is a part of a novel gene having homology to the ATP synthase delta chain. The obtained nucleotide sequence information is respectively shown in SEQ ID NO: 13 and SEQ ID NO: 14 in Sequence Listing. In addition, each of these nucleotide sequences encodes the polypeptide having the amino acid sequence shown in SEQ ID NO: 4 or SEQ ID NO: 5 in Sequence Listing.

Also, four clones comprising a part of a known cDNA of the HSP70 SSB type were obtained, each being cDNA encoding 294 amino acids, 162 amino acids, 118 amino acids, and 101 amino acids of the C-terminus side, respectively. As a result, it was clarified that the HSP70 SSB type antigen has an antigenic determinant reactive to the antiserum within the region consisting of 118 amino acid of the C-terminus side. The nucleotide sequence of the HSP70 SSB type gene encoding the longest 294 amino acids, and the amino acid sequence deduced therefrom are as shown in SEQ ID NO: 18 and SEQ ID NO: 9, respectively.

Next, there existed phage plaques which were positive against the absorption antiserum obtained by addition of HSS but negative against the above absorption antiserum obtained by addition of the HSS and the CW. The cDNAs of these plaques were analyzed in the same manner as in item 2) above. Two clones comprised a full length of a novel gene having homology to the S. cerevisiae BMH 2 gene. One clone comprised a nearly full length of another novel gene having homology to the S. cerevisiae ribosomal protein L7 gene. Another one clone contained a part (115 amino acids) of a novel gene having homology to S. cerevisiae YNL 083W.

The nucleotide sequences of these novel genes, i.e., the S. cerevisiae BMH 2 homologue gene, the S. cerevisiae ribosomal L7 protein homologue gene, and the S. cerevisiae YNL 083W homologue gene, are respectively shown in SEQ ID NO: 15, SEQ ID NO: 16, and SEQ ID NO: 17 in Sequence Listing. From the above nucleotide sequences, each of these genes encodes the polypeptide having the amino acid sequences respectively shown in SEQ ID NO: 6, SEQ ID NO: 7, or SEQ ID NO: 8 in Sequence Listing.

Example 4

Production of Antigenic Proteins Which Were Recognized by Antisera from Mammals Having C. albicans Infection Resistance The cDNAs obtained in items 2) and 3) of Example 3, except the gene having homology to S. cerevisiae YNL 083W, expressed genes as fusion proteins. The gene having homology to YNL 083W expressed a polypeptide from the initiation codon (ATG) in the cDNA. As an example of the expression of a fusion protein, polypeptides expressed from a gene having homology to triosephosphate isomerase (TPI) and from a gene having homology to lysyl-tRNA synthase were clarified.

Specifically, a plasmid carrying the gene having homology to TPI (triose phosphate isomerase) obtained in item 2) of Example 3, and a plasmid carrying the gene having homology to lysyl-tRNA synthase, were each transformed into Escherichia coli BL21(DE3)pLysS to give transformants. Each of these transformants was inoculated to LB medium containing ampicillin, and cultured at 37° C. for 3.5 hours. IPTG (isopropyl-1-thio-β-D-galactoside) was added to the resulting culture so as to have a final concentration of 1 mM, and thereafter the culture was continued for additional 2.5 hours. The culture was centrifuged to harvest the cells, and the cells were washed and suspended in 30 µl of 1×SDS sample buffer. The suspension was subjected to heat treatment at 100° C. for 5 minutes, and thereafter the suspension was centrifuged. A part of the supernatant was subjected to SDS-polyacrylamide gel (12.5% gel) electrophoresis, thereby confirming the expression of a polypeptide.

The deduced molecular weights of the expressed fusion proteins are 63 kDa (27 kDa for TPI (triose phosphate isomerase) homologue +36 kDa for T7 tagged region) for the TPI (triose phosphate isomerase) homologue, and 50 kDa (14 kDa for lysyl-tRNA synthetase homologue +36 kDa for T7 tagged region) for the lysyl-tRNA synthetase homologue. FIG. 1 clearly showed that these fusion proteins are expressed as polypeptides having the respective deduced molecular weights.

The sample of lane 1 in FIG. 1 is a polypeptide obtained before the induction of expression of the transformant in which the lysyl-tRNA synthase homologue gene (before addition of IPTG) was transduced; and the sample of lane 2 is a polypeptide obtained after the induction (after addition of IPTG). The sample of lane 3 comprises the polypeptide obtained before the induction of expression of the transformant in which the TPI homologue gene was transduced, and the sample of lane 4 is the polypeptide obtained after the induction.

INDUSTRIAL APPLICABILITY

The antigenic protein of the present invention is an antigenic protein which is recognized by antiserum derived from a mammal having Candida albicans-infection resistance, so that the antigenic protein is useful for treatment and diagnosis of Candida albicans-infection. The nucleic acid of the present invention is that encoding the antigenic protein of the present invention, so that the nucleic acid is useful for treatment and diagnosis of Candida albicans-infection.

What is claimed is:

1. An isolated antigenic polypeptide which is recognized by an antiserum from a mammal having resistance to *Candida albicans* infection, wherein said antigenic polypeptide is:
   - (A) a polypeptide having the amino acid sequence of SEQ ID NO: 1;
   - (B) a polypeptide encoded by a nucleic acid having the nucleotide sequence of SEQ ID NO: 10; or
   - (C) a polypeptide encoded by a nucleic acid capable of hybridizing with a nucleic acid which encodes a polypeptide having the amino acid sequence of SEQ ID NO: 1, or a nucleic acid having the nucleotide sequence of SEQ ID NO: 10, or a nucleic acid fully complementary thereto, under stringent conditions which include incubation at 50° C. for 12 to 20 hours together with a nucleic acid probe in 6×SSC, wherein 1×SSC has 0.15M NaCl, 0.015M sodium citrate and a pH of 7.0 and contains 0.5% by weight of SDS, 0.1% by weight of bovine serum albumin, 0.1% by weight polyvinyl pyrrolidone, 0.1% by weight of a synthetic, water soluble, nonionic copolymer of sucrose and epichlorhydrin having a molecular weight of about 400,000, and 0.01% by weight of denatured salmon sperm DNA.

2. An isolated nucleic acid encoding an antigenic polypeptide which is recognized by an antiserum from a mammal having resistance to *Candida albicans* infection, wherein said nucleic acid is:

(A) a nucleic acid encoding polypeptide having the amino acid sequence of SEQ ID NO: 1;

(B) a nucleic acid having the nucleotide sequence of SEQ ID NO: 10; or (C) a nucleic acid capable of hybridizing with the nucleic acid according to (A) or (B), or a nucleic acid fully complementary thereto, under stringent conditions which include incubation at 50° C. for 12 to 20 hours together with a nucleic acid probe in 6×SSC, wherein 1×SSC has 0.15M NaCl, 0.01 5M sodium citrate and a pH of 7.0 and contains 0.5% by weight of SDS, 0.1% by weight of bovine serum albumin, 0.1% by weight polyvinyl pyrrolidone, 0.1% by weight of a synthetic, water soluble, nonionic copolymer of sucrose and epichlorhydrin having a molecular weight of about 400,000, and 0.01% by weight of denatured salmon sperm DNA.

3. A vector comprising the nucleic acid of claim 2.

4. An isolated transformant selected from the group consisting of insect cells, animal cells, bacteria, yeasts and fungi resulting from transformation with the vector of claim 3.

5. A pharmaceutical composition comprising the antigenic polypeptide of claim 1.

6. A diagnostic composition comprising the antigenic polypeptide of claim 1.

7. A pharmaceutical composition comprising the nucleic acid of claim 2.

8. A diagnostic composition comprising the nucleic acid of claim 2.

9. An isolated nucleic acid capable of specifically binding to the nucleic acid of claim 2.

10. The antigenic polypeptide of claim 1 which is isolated from fungi other than *Saccharomyces cerevisiae*.

11. The antigenic polypeptide of claim 10 which is isolated from the fungi belonging to the genus *Candida*.

12. The nucleic acid of claim 2 which is isolated from fungi other than *Saccharomyces cerevisiae*.

13. The nucleic acid of claim 12 which is isolated from the fungi belonging to the genus *Candida*.

14. The antigenic polypeptide of claim 1, wherein said stringent conditions further include subsequent washing initiated at a temperature of 37° C. in 2×SSC containing 0.5% by weight of SDS, the SSC concentration being variable up to a range of 0.1×SDS and the temperature being variable up to a range of 50° C.

15. The isolated nucleic acid of claim 2, wherein said stringent conditions further include subsequent washing initiated at a temperature of 37° C. in 2×SSC containing 0.5% by weight of SDS, the SSC concentration being variable up to a range of 0.1×SDS and the temperature being variable up to a range of 50° C.

* * * * *